United States Patent [19]

Kater et al.

[11] Patent Number: 5,145,565
[45] Date of Patent: Sep. 8, 1992

[54] CONTAMINATION-FREE METHOD AND APPARATUS FOR MEASURING BODY FLUID CHEMICAL PARAMETERS

[75] Inventors: John Kater, Santa Ana, Calif.; Glenn Pelikan, Portland, Oreg.

[73] Assignee: SpaceLabs, Inc., Redmond, Wash.

[21] Appl. No.: 346,138

[22] Filed: May 1, 1989

[51] Int. Cl.⁵ .......................................... G01N 27/00
[52] U.S. Cl. .......................... 204/153.1; 204/153.12; 204/416; 204/400; 204/403; 436/8; 436/809; 604/403; 604/410; 604/318
[58] Field of Search .......... 204/153.1, 153.12, 153.15, 204/153.17, 153.18, 416, 400, 403; 604/318, 319, 403, 410, 8; 436/809

[56] References Cited

U.S. PATENT DOCUMENTS

| | | | |
|---|---|---|---|
| 3,639,829 | 2/1972 | Harnoncourt | 204/153.17 |
| 4,200,493 | 4/1980 | Wilkins et al. | 204/153.12 |
| 4,339,317 | 7/1982 | Meiattini et al. | 204/403 |
| 4,654,127 | 3/1987 | Baker et al. | 204/416 |
| 4,753,775 | 6/1988 | Ebersok et al. | 436/809 |
| 4,762,594 | 8/1988 | Guruswamy | 204/153.1 |
| 4,856,533 | 8/1989 | Anraku et al. | 604/403 |
| 4,872,956 | 10/1989 | Kotani et al. | 436/8 |

FOREIGN PATENT DOCUMENTS 306158 9/1988 European Pat. Off. .
317847 11/1988 European Pat. Off. .

Primary Examiner—John Niebling
Assistant Examiner—Arun Phasge
Attorney, Agent, or Firm—Seed and Berry

[57] ABSTRACT

A sample of a body fluid, such as blood, is collected in a cartridge having a sample chamber for storing the sample and one or more calibration chambers, each for storing a respective calibration fluid. The fluid sample is drawn ino the sample chamber by placing the sample chamber in fluid communication with a needle inserted into the fluid sample and applying a vacuum to the chamber using either a syringe or internal vacuum. A body fluid sample may also be drawn into the sample chamber from a syringe or capillary tube containing the fluid sample. The cartridge may be either planar or cylindrical. The chambers of a cylindrical cartridge may be either elongated voids symmetrically positioned about the longitudinal axis of the cartridge or axially spaced annular voids. One or more sensors, such as ion-sensitive electrodes, are placed in contact with the fluid sample and calibrating fluids(s) by either placing the sensor(s) in contact with externally accessible chambers or by allowing the fluid sample and calibrating fluid(s) to flow from the chambers past the sensor(s). In the event that the sensor(s) are placed in direct contact with externally accessible chambers, the sensor(s) may be scanned from one chamber to the next by an automatic drive mechanism.

55 Claims, 20 Drawing Sheets

CONTAMINATION-FREE METHOD AND APPARATUS FOR MEASURING BODY FLUID CHEMICAL PARAMETERS

FIELD OF THE INVENTION

This invention relates to the field of medical testing instruments, and more particularly, to a method and apparatus for collecting and analyzing body fluids, such as blood samples, in a manner that prevents the fluid from either becoming contaminated or contaminating medical personnel during the collecting or analyzing process.

BACKGROUND ART

It is often necessary in the field of medicine to determine the chemical composition of body fluids in animals and humans. For example, it is often necessary to determine the chemical composition of blood in order to diagnose various diseases or determine the condition of a patient. Blood is typically drawn from a patient by puncturing a vein or artery with a needle and then drawing the blood into either a syringe or a "VACUTAINER." A "VACUTAINER" is a device consisting of two components, namely, an adapter having a double-ended needle and an evacuated test tube sealed with a resilient cap. The "VACUTAINER" is used by first inserting one end of the needle into a patient's blood vessel and then puncturing the test tube's resilient end cap with the other end of the needle. The vacuum in the test tube then draws blood through the needle and into the test tube. After sufficient blood has been drawn into the test tube, the needle is removed from the cap and the patient's blood vessel. The resiliency of the cap causes the puncture through the cap to be sealed to prevent blood from leaking from the test tube and to prevent additional air from being drawn into the test tube.

After the blood has been drawn from the patient, it is sent to a laboratory for processing. If the blood was drawn with a syringe, the needle is removed from the syringe and discarded before the syringe is sent to the lab. If the blood was drawn with a "VACUTAINER", the "VACUTAINER" adapter is discarded and the test tube is sent to the lab.

The above-described procedures are representative of the procedures followed in most hospitals and other health care institutions. Although such procedures are very common, they are not without serious problems that can adversely affect the cost and safety of providing and receiving health care. The delay inherent in sending blood samples to a central lab can prevent prompt reporting of the test results. Under some circumstances, this delay can pose a serious threat to the health and safety of a patient since it may be necessary to delay corrective drug treatment or other procedures until the test results have been received. The need to send a patient's blood sample to a location where a large number of other samples are being sent raises the obvious possibility that the patient's sample will become lost or incorrectly identified. Under these circumstances, an abnormality in the patient's blood could become misidentified with another patient so that the abnormality would go untreated. Also, the patient could receive treatment indicated by a lab report resulting from tests on another patient's blood, and such treatment would be wasteful and possibly harmful.

The disadvantages of the above, commonly used lab test procedures extend not only to the manner in which the blood samples are processed but also to the manner in which the blood samples are obtained. In the case of blood samples obtained using a syringe, the health care practitioner all to often sticks himself or herself with the needle as it is being removed from the syringe. Needle sticks caused in this manner can expose the practitioner to serious and even fatal diseases. The patient's blood sample can also contaminate the health care practitioner or lab technician when the blood sample is being transported to the lab or transferred from the syringe or test tube to another container.

Current blood test procedures also provide an avenue for various errors or inaccuracies to enter into the testing procedure. For example, blood can be transferred from the syringe or test tube into a container that has been improperly or insufficiently cleaned. As a result, the blood sample can become contaminated with residue left in the container, thereby affecting the accuracy of tests performed on the sample. Contaminants can also be present in the chemical analysis instruments that process the blood sample since the sample comes into contact with the same tubes, valves, pumps, etc., that the blood samples of other patients contact. In fact, it is quite common for deposits to build up in the flow path of the analysis instrument. These deposits provide a ready vehicle for the growth of bacteria and the retention of blood samples or calibrating fluids from one sample to the next. Deposits on such components as valves can also cause them to stick either open or shut. While such flow path components as tubing, valves and pumps can be replaced whenever deposits start to build, frequent replacement of such components can be very expensive. The need to frequently monitor the condition of, and replace the components of, conventional blood chemical analyzing instruments can also be very time-consuming and thus diverts the attention of health care practitioners from the care of patients.

Most of the above-described problems of conventional testing procedures could be eliminated if the blood sample was analyzed using a disposable instrument located at the patient's bedside. However, bedside blood analysis was heretofore thought not to be practical because the high cost of conventional blood analysis instruments prevented them from being either disposable or used in the large numbers required for beside analysis.

DISCLOSURE OF THE INVENTION

It is an object of the invention to provide a method and apparatus for collecting body fluid samples in a manner that prevents them from either becoming contaminated or contaminating health care practitioners.

It is another object of the invention to provide a method and apparatus for collecting body fluid samples in which the body fluid need not be transferred from a collection device to another container in order to be analyzed.

It is another object of the invention to provide a system for collecting and analyzing body fluid samples in which all components of the system that come into contact with a patient are relatively inexpensive and may thus be disposable and used in large numbers.

It is still another object of the invention to provide a system for collecting and analyzing body fluid samples which does not repetitively expose internal components to be samples, thereby preventing cross contamination between samples, minimizing maintenance requirements, and preventing the buildup of deposits and the growth of bacteria on internal components.

It is a further object of the invention to provide a system for collecting and analyzing body fluid samples that can be adapted to analyze a wide variety of chemical parameters.

These and other objects of the invention are provided by a method and apparatus for obtaining and analyzing a body fluid sample using a sample collection cartridge and an ion-selective electrode or other sensor in physical or optical communication with the sample while it is in the cartridge. The cartridge includes a sample chamber communicating with a first externally accessible fluid port and a calibrating chamber contain a calibrating fluid. A body fluid sample, such as blood, is drawn into the sample chamber through the first externally accessible fluid port by a variety of means. The sample may be drawn into the cartridge using a syringe by mounting a needle and a syringe on the cartridge in fluid communication with the sample chamber and then drawing the sample into the sample chamber with the syringe. The body fluid sample may also be drawn into the cartridge by evacuating one or more sample chambers so that the suction in the sample chamber(s) draws the fluid sample directly into the chamber(s). The sample chamber and the calibrating chamber may be externally accessible so that the sensors can be sequentially placed in each of the chambers. Alternatively, the body fluid and calibrating fluid can be withdrawn from the cartridge with a needle and allowed to flow past the sensor. The cartridge may be either generally planar or cylindrical. A cylindrical cartridge having a partially evacuated sample chamber may be sized to fit into a conventional "VACUTAINER" adapter so that it can be used to collect blood in the same manner that an adapter is conventionally used to collect a blood sample in an evacuated test tube.

BEST MODE FOR CARRYING OUT THE INVENTION

Figures 1, 2:
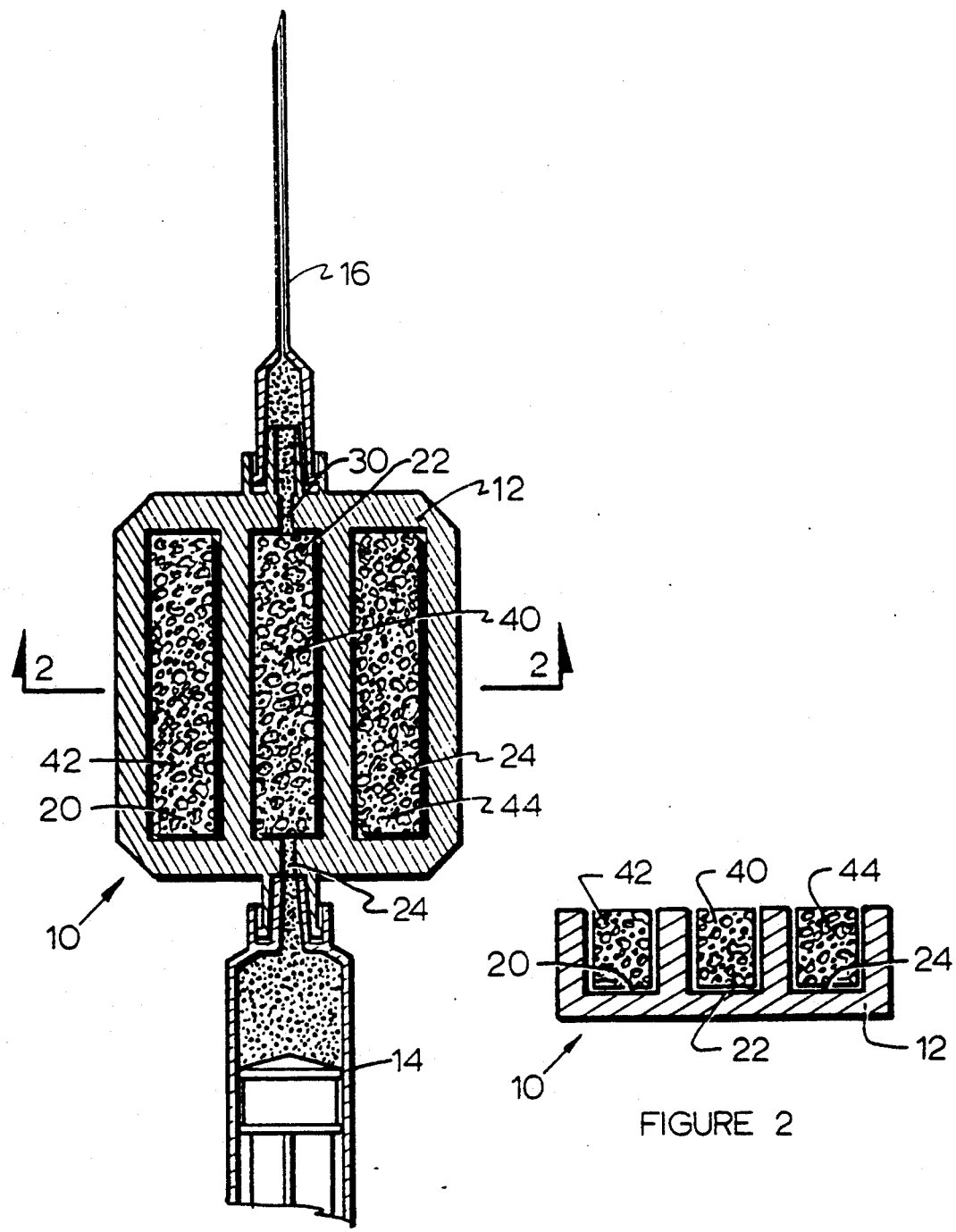
FIG. 1 is a top plan view of one embodiment of a cartridge for obtaining and collecting a body fluid sample in a contamination-free manner.
FIG. 2 is a cross-sectional view taken along the line 22 of FIG. 1.

One embodiment of a device for collecting body fluid samples and allowing the samples to be analyzed in the collection device is illustrated in FIGS. 1 and 2. The embodiment of FIGS. 1 and 2, like the subsequently described embodiments, is described as being used to obtain blood samples. However, it will be understood that the embodiments described herein can be advantageously used to collect and analyze virtually any body fluid under circumstances where contamination of the sample, other patients or medical personnel is possible.

With reference to FIGS. 1 and 2, the device 10 comprises a cartridge 12 connected between a conventional syringe 14 and a conventional hypodermic needle 16. The syringe 14 and needle 16 are connected to the cartridge 12 through conventional Luer lock connectors. The cartridge 12 is of a substantially planar, rectangular configuration having three elongated chambers 20, 22, 24 formed therein. The center chamber 22 is connected to the syringe 14 through a conduit 28 and to the hypodermic needle 16 through conduit 30. The end chambers 20, 24 are isolated from both the syringe 14 and needle 16.

The center chamber 22 is preferably but not necessarily filled with an absorbent material 40 so that when the syringe 14 draws blood through the needle 16, the blood will saturate the absorbent material 40. The other chambers 20, 24 also preferably contain absorbent materials 42, 44 which are soaked with respective calibration solutions to calibrate the blood chemical measuring instrument, as explained in greater detail below. The purpose of the absorbent material 4044 is thus to contain or provide physical stability for the blood sample or calibrant.

Figure 3:
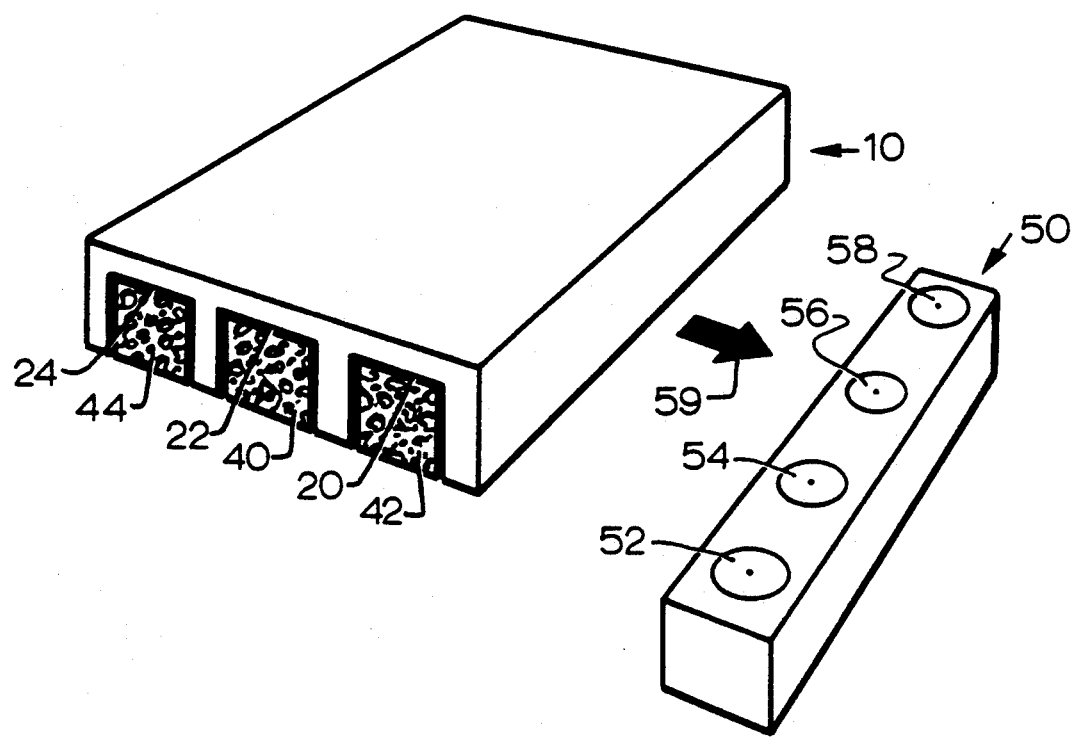
FIG. 3 is a mechanical schematic illustrating the manner in which a fluid sample collected using the cartridge shown in FIGS. 1 and 2 is analyzed.
Figure 35:
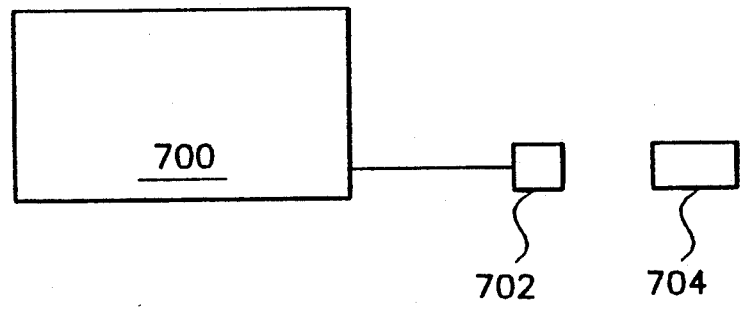
FIG. 35 is a schematic showing a conventional body fluid analyzer interfacing with the inventive body fluid sample cartridge.

The manner in which the blood collected in the cartridge 12 is analyzed is illustrated in FIG. 3. The cartridge 10 is drawn across a sensor array 50 which may consist of a single sensor or a plurality of sensors 52 58, each of which is selective to a different blood chemical or parameter. The cartridge is drawn across the sensor array 50 in the direction indicated by the arrow 59 until the absorbent material 42 in chamber 20 is positioned above the sensor array 50, with the absorbent material 42 making contact with the sensors 52, 58. As mentioned above, the absorbent material 42 contains a conventional calibrant that is used to calibrate the sensors 52, 58 and the circuitry connected to the sensors (not shown). After the analyzing instrument has been calibrated, the cartridge 10 is moved in the direction of the arrow so that the absorbent material 40 containing the blood sample is placed against the sensors 52, 58. The sensors 52, 58 then measure various blood chemical parameters as determined by the ion selectivity of the sensors 52, 58. After the chemical composition of the blood has been analyzed, the cartridge 10 is moved another step in the direction of the arrow until the absorbent material 44 is placed against the sensors 52, 58. As mentioned above, the absorbent material 44 contains a second conventional calibrating fluid 44 that is used to define a second calibration point for the analyzing system. The use of two calibration points allows both the slope and the offset of the calibration curve to be determined along with the location of each chemical parameter on that calibration curve, thereby improving the accuracy of the measurement. The sensors 52, 58 may be, for example, conventional ion-selective electrodes. However, other types of conventional sensors, such as conductance, fiberoptic or amperometric sensors, may be used. For example, as illustrated in FIG. 35, a conventional body fluid analysis device 700 includes a conventional sensor 702 adapted to contact a body fluid sample in one embodiment of the inventive cartridge 704. Conventional electronic circuitry in the analysis device 700 is connected to the sensor 702 for providing an electrical indication of the value of the body fluid parameter being measured.

Figures 4, 5:
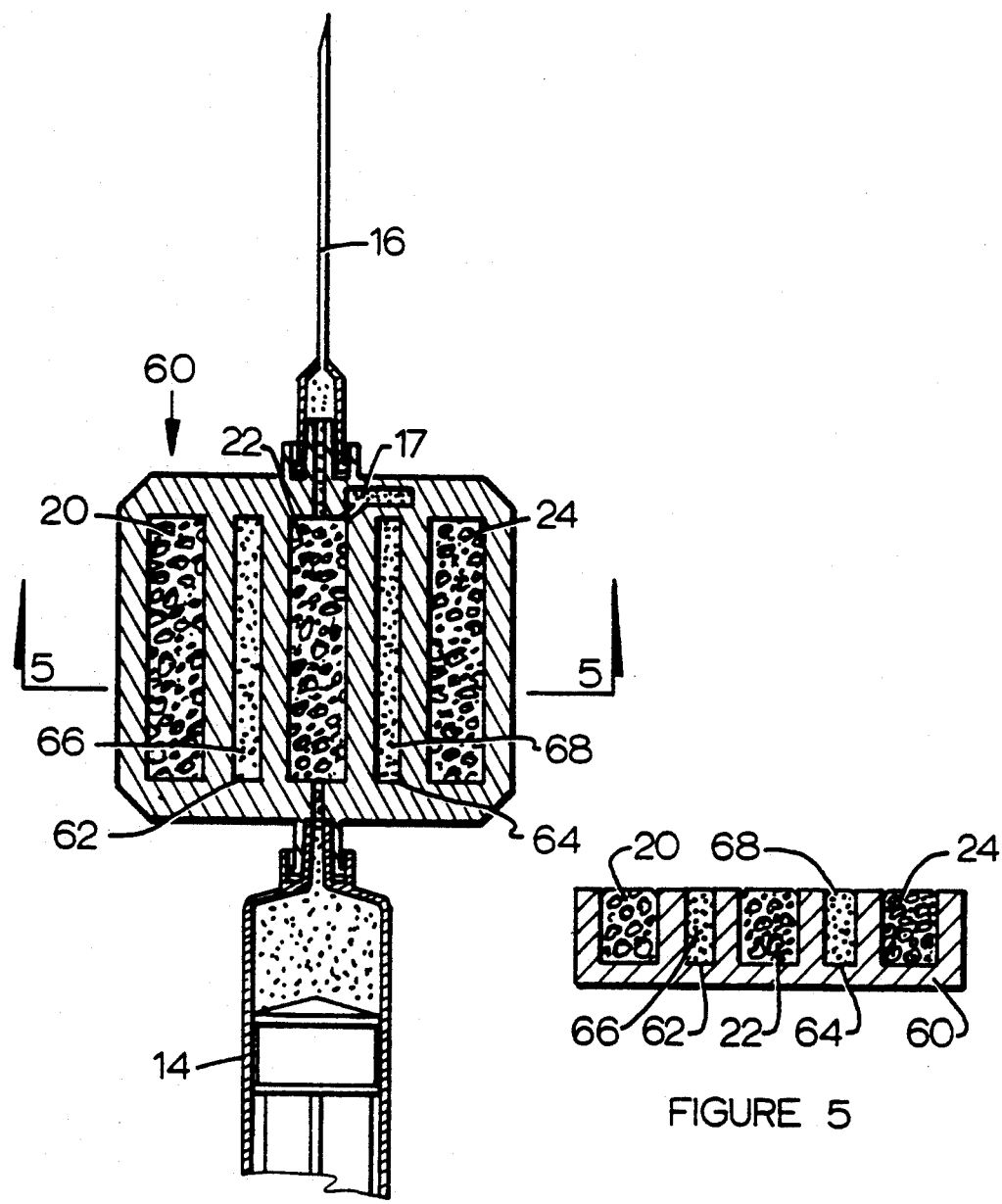
FIG. 4 is a top plan view of another embodiment of a cartridge for obtaining and collecting a body fluid sample in a contamination-free manner.
FIG. 5 is a cross-sectional view taken along the line 55 of FIG. 4.

Another embodiment of the inventive blood collection device is illustrated in FIGS. 4 and 5. This embodiment of the collection device 60 is substantially the same as the embodiment illustrated in FIG. 2 except that it includes additional chambers 62, 64 filled with an absorbent material 66, 68. The absorbent material 66, 68 in the chambers 62, 64 is not saturated with a calilbrant, nor does it collect the blood sample. Instead, the absorbent material 66, 68 in the chambers 62, 64 is used to absorb any residue of the calibrant or blood sample left on the sensor array 50 (FIG. 3) as the collection device 60 is drawn across the sensor array 50. The absorbent materials 66, 68, serving as blotters, prevent the carry over of residue from one measuring point to the next, thereby improving the accuracy of the readings.

Figure 6:
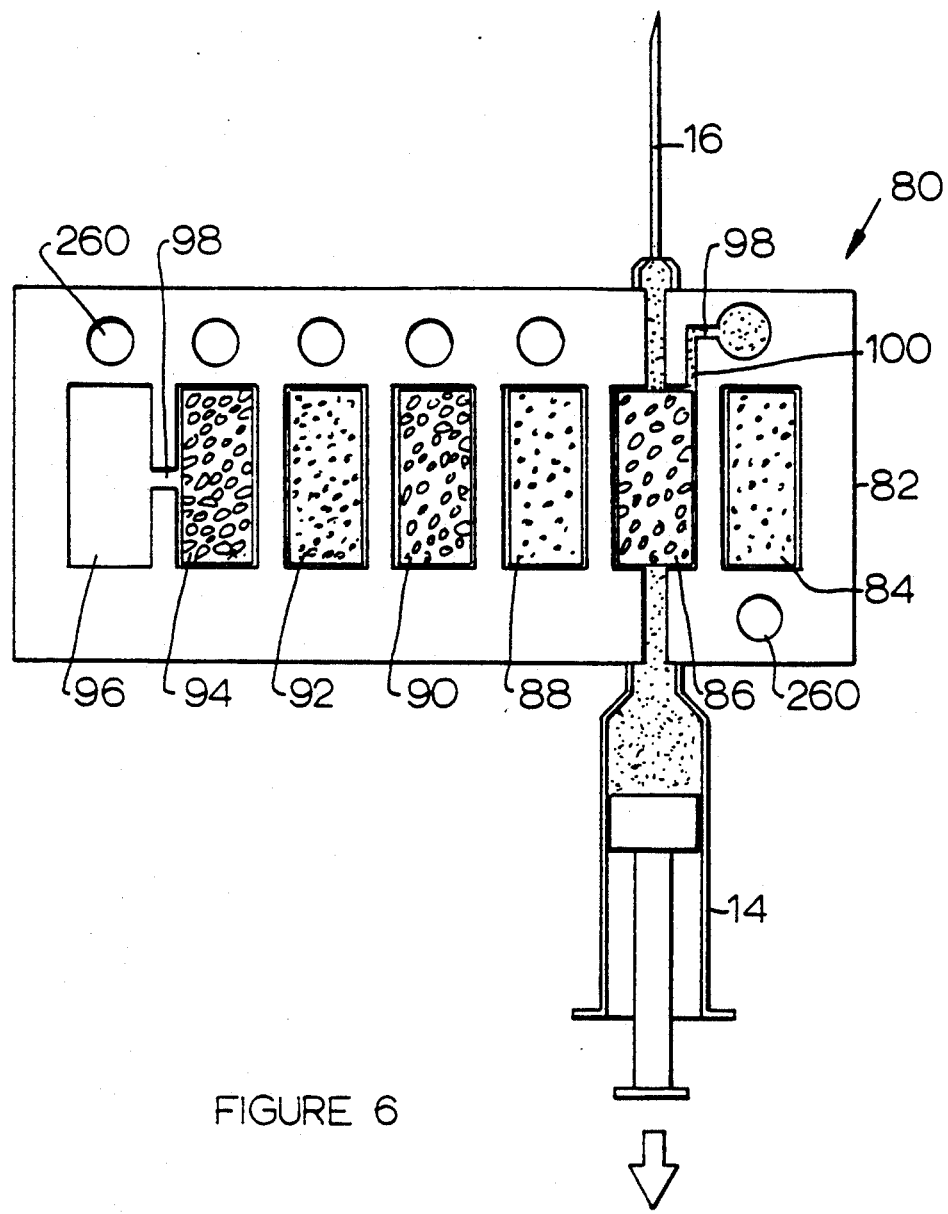
FIG. 6 is a top plan view of another embodiment of a cartridge for obtaining and collecting a body fluid sample in a contamination-free manner.

Still another embodiment of a blood collecting cartridge is illustrated in FIG. 6. The cartridge 80 differs from the previously described cartridges primarily in the number of chambers formed therein. The cartridge 80 illustrated in FIG. 6 includes a body portion 82 having seven generally elongated chambers 84, 96 formed therein. Chambers 84, 88 and 92 contain a dry absorbent material so that the chambers 84, 88, 92 serve as blotters. Chamber 86 contains a dry absorbent material. However, since the chamber 86 forms a passage between the syringe 14 and needle 16, the absorbent material in the chamber 86 becomes saturated with the blood sample. A vent 98 communicates with the chamber 86 through a capillary path 100. The vent 98 allows air to escape from the sample chamber 86 as it is being filled with the blood sample. Chambers 90 and 94 are filled with an absorbent material saturated with respective calibrant fluids. Chamber 96 is a reservoir filled with a calibrating fluid. The chamber 96 is connected to chamber 94 through a wick 98.

The cartridge 80 may be used with a sensor array 50, as illustrated in FIG. 3. Chamber 84 is first brought into contact with the array 50 in order to absorb any blood or calibrating fluid remaining after the previous blood test. The chamber 86 containing the blood sample then makes contact with the sensor array 50 in order to analyze the chemical parameters of the blood. After the chemical parameters of the blood have been analyzed, the cartridge 80 is moved an additional step across the sensor array 50 so that the absorbent material in chamber 88 absorbs the blood on the sensor array 50. Chamber 90, containing the calibrating fluid, is then placed in contact with the sensor array to determine one calibration point of the analyzing instrument connected to the sensor array. Fluid residues on sensor array 50 are then absorbed by the material in the chamber 92, and the cartridge 80 is moved so that the calibrating fluid in chamber 94 makes contact with a blotted sensor array 50. After the second calibration point has been established, the cartridge remains stationary until a subsequent test is to be conducted. The calibrating fluid in the chamber 94 continuously maintains the sensors 52, 58 wet in order to optimize their performance for a subsequent analysis. The calibrating fluid reservoir 96, connected to chamber 94 via a porous wick, prolongs the wetting of the surfaces of the sensors in sensor array 50 to ensure optimal sensing conditions from one cartridge to another.

Figure 7:
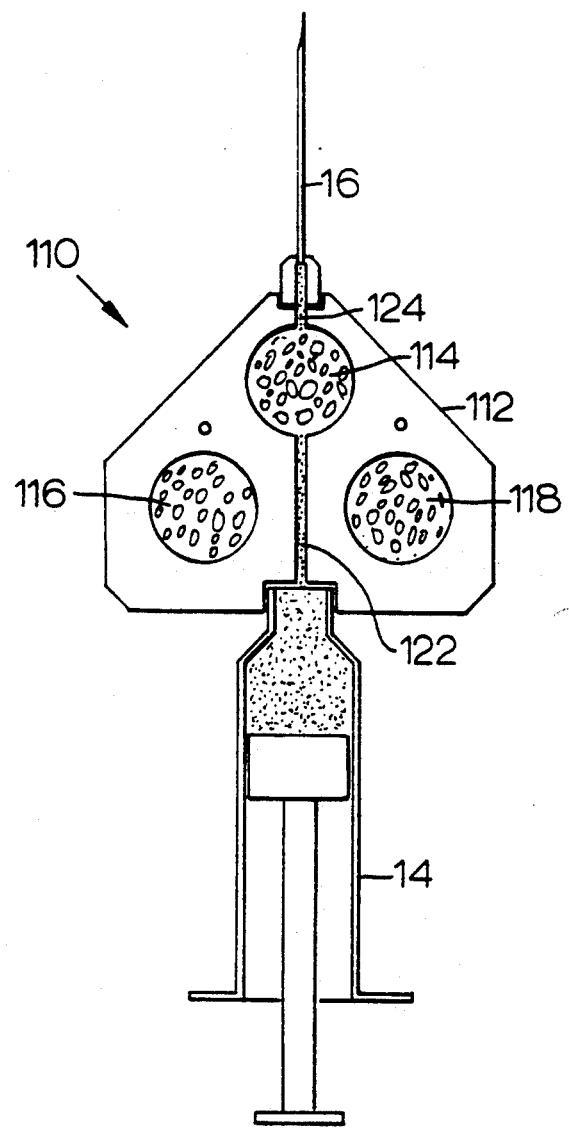
FIG. 7 is a top plan view of still another embodiment of a cartridge for obtaining and collecting a body fluid sample in a contamination-free manner.

Another embodiment of a blood collection cartridge 110 is illustrated in FIG. 7. The cartridge 110 includes a cartridge body 112 having formed therein three cylindrical chambers 114, 116, 118. Chambers 116, 118 are filled with an absorbent material saturated with respective calibrating fluids. Chamber 114 is connected between the syringe 14 and needle 16 through passages 122, 124. Blood is drawn through the needle 16 into the syringe 14, thereby passing through the chamber 114 and saturating the absorbent material contained therein to collect the blood sample. The blood sample in the cartridge 110 is analyzed by sequentially placing the chambers 118, 114, 116 in contact with a sensor or array of sensors arranged in a circle. The chamber 118 is first placed in contact with the sensor(s) to obtain one calibration point for the analyzing system. The sensor(s) are then placed in contact with the blood sample in the chamber 114 to obtain a chemical analysis of the blood. Finally, the sensor(s) are placed in contact with the calibrating fluid in the chamber 116 to obtain a second calibration point for the analyzing instrument.

Figure 8:
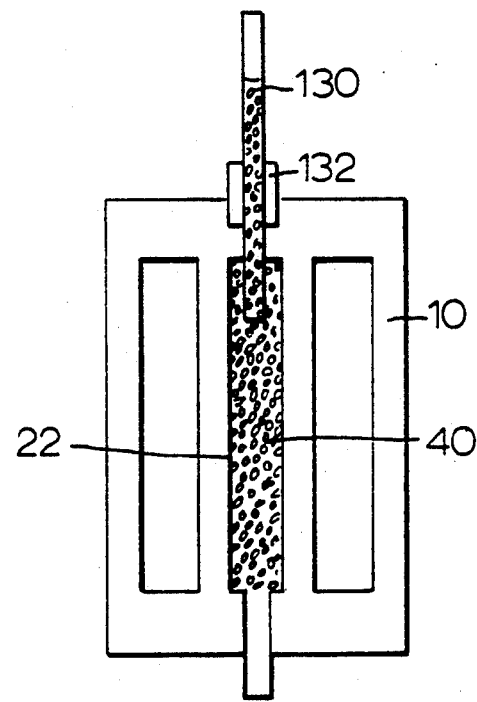
FIG. 8 is a top plan view of the collection cartridge of FIGS. 1 and 2 showing an alternate technique for collecting a body fluid sample in the cartridge.

The previously described blood collection cartridges are placed between a syringe 14 and a needle 16 in order to obtain the blood sample. However, blood may be placed in the blood sample chamber through other means. For example, as illustrated in FIG. 8, a capillary tube 130 may be filled with blood by pricking the finger of a patient and placing the end of the capillary tube against the puncture site and allowing the blood to flow into the tube. The capillary tube 130 is then inserted through the hole of syringe adapter 132 so that the end of the capillary tube 130 makes contact with the absorbent material 40 in the chamber 22. The absorbent material then draws the blood from the capillary tube 130.

Figure 9:
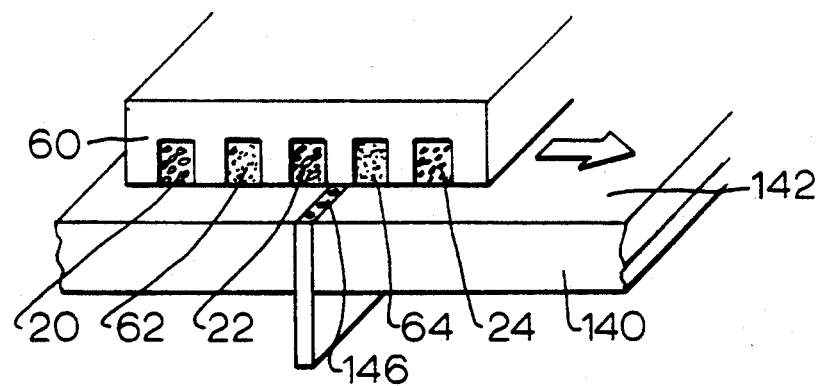
FIG. 9 is a mechanical schematic illustrating one technique for analyzing a body fluid sample collected using the cartridge shown in FIGS. 4 and 5.

The collection device 60, illustrated in FIGS. 4 and 5, is shown being analyzed in FIG. 9. The collection device 60 is placed on a base 140 having a planar upper surface 142. A sensor array 144 containing a plurality of sensors, generally indicated at 146, is mounted in the base, with the sensors 146 flush with the upper surface 142 of the base 140. The cartridge 60 is scanned across the electrodes 146 from left to right, thereby sequentially exposing the chambers 24', 64, 22', 62, 20' to the sensors 146. The cartridge 60 is preferably drawn away from the surface 142 of the base 140 as it moves along the surface 142 in order to prevent the blood sample and calibrating fluids from smearing the surface 142.

Figure 10:
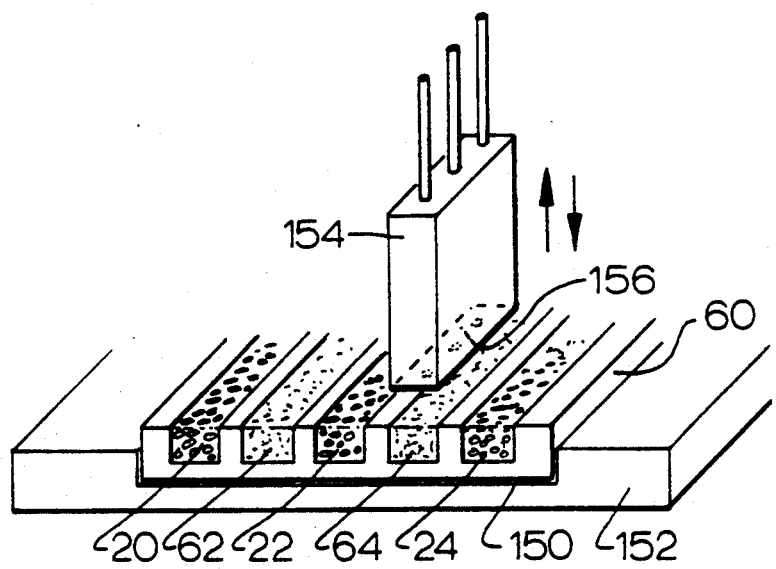
FIG. 10 is a mechanical schematic illustrating another technique for analyzing a body fluid sample collected using the cartridge shown in FIGS. 4 and 5.

In the embodiment of FIG. 9, the base 140 is stationary and the cartridge 60 is scanned across the base so that the sensors 146 make contact with each of the chambers. However, it will be apparent that, since only relative movement between the sensor array 144 and the cartridge 60 is required, the cartridge 60 may be maintained stationary while the sensor array is scanned across the cartridge 60. With reference to FIG. 10, the cartridge 60 is placed in a rectangular recess 150 formed in a base 152. A sensor assembly 154 containing a plurality of sensors on face 156 is then sequentially placed against each chamber 24', 64, 22', 62, 20' of the cartridge 60. The sensor assembly 154 is preferably drawn away from the cartridge 60 as it moves from one chamber to the next in order to prevent the sensor assembly 154 from smearing calibrating fluid or blood from one chamber to the next.

Figure 11A:
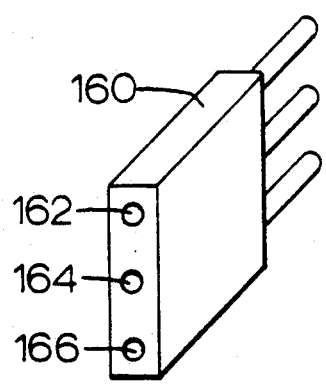
FIGS. 11A and 11B are isometric views of two sensor assembly designs that can be used to analyze body fluid samples collected in the inventive blood collecting cartridges.
Figure 11B:
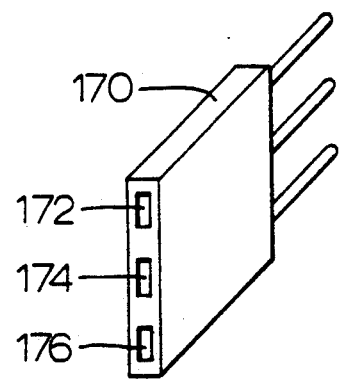

Two examples of sensor assemblies are shown in FIGS. 11A and 11B. The sensor assembly 160, shown in FIG. 11A, utilizes three circular sensors 162, 166, each of which is, in the embodiment illustrated, coated with an ion selective membrane. Similarly, the sensor assembly 170, illustrated in FIG. 11B, has formed therein three sensors 172, 176 having a rectangular configuration. Each of the sensors 172, 176 is covered by an ion selective membrane so that the sensors 172, 176 are selective to specific ions in the blood sample. Sensors other than ion selective electrodes may also be used to measure blood constituents.

Figure 12:
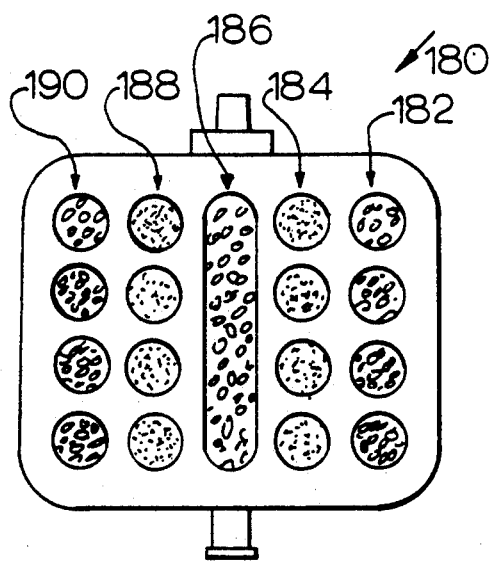
FIG. 12 is a top plan view of another embodiment of a cartridge for obtaining and collecting a body fluid sample in a contamination-free manner.

In the previously illustrated embodiments of the inventive blood collection cartridge, the same calibrating fluid is used for each sensor of a sensor assembly. However, it may be desirable to utilize different calibrating fluids for different sensors, measuring different parameters. Accordingly, a blood collection cartridge 180, illustrated in FIG. 12, utilizes separate cylindrical chambers which may contain absorbent material. More specifically, as illustrated in FIG. 12, cylindrical chambers 182 each contain a respective calibrating fluid, although the calibrating fluid may not be the same for all cylindrical chambers. Cylindrical chambers 184 are used to blot the residual calibrating fluid remaining on the surface of the sensors before they come in contact with the sample in sample chamber 186. Chambers 188 contain dry absorbent material to absorb blood residues from the sensors, and chambers 190 contain respective second calibrating fluids which may or may not be identical to each other to establish a second calibration point. It will be understood that the chambers illustrated in the collection cartridge 180 of FIG. 12 may also be used for other purposes. For example, the chambers 182, 184 may contain respective calibration fluid, the chambers 188 may contain a washing fluid to clean the sensors, and chamber 190 may contain a dry absorbent material to dry the sensors before a subsequent collection cartridge 180 makes contact with the sensors.

Figure 13:
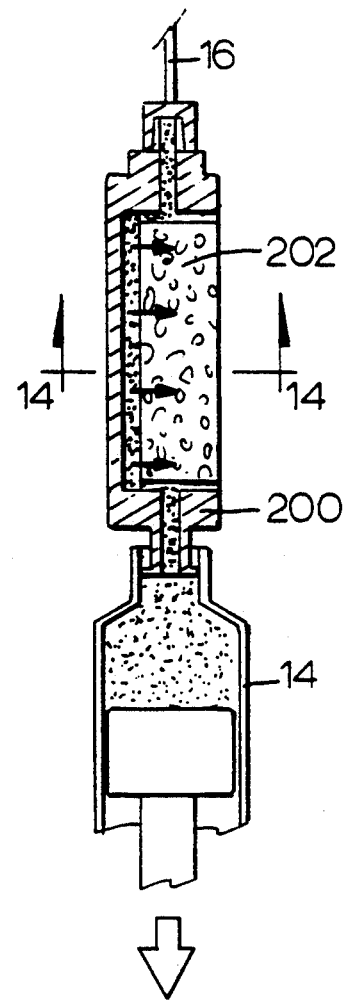
FIG. 13 is a longitudinal cross-sectional view of one embodiment of a cartridge for obtaining and collecting a body fluid sample shown being used to collect a fluid sample with a syringe.
Figure 14:
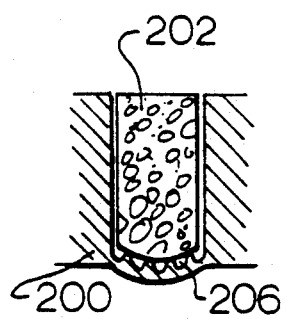
FIG. 14 is a cross-sectional view taken along the line 1414 of FIG. 13.

The previously described embodiments of the blood collection cartridge each utilize a blood sample chamber that extends directly between two conduits which are generally used to connect the cartridge between a needle and syringe. However, as illustrated in FIGS. 13 and 14, a syringe 14 and needles 16 may be connected to each other by a passage 200 that bypasses a collection chamber 202 for the blood sample. However, the passage 200 is in fluid communication with the chamber 202 through multiple conduits or capillaries 206, best illustrated in FIG. 14. As the blood flows through the passage 200 from the needle 16 to the syringe 14, the absorbent material in the chamber 202 draws blood from the capillaries 206.

Figure 15:
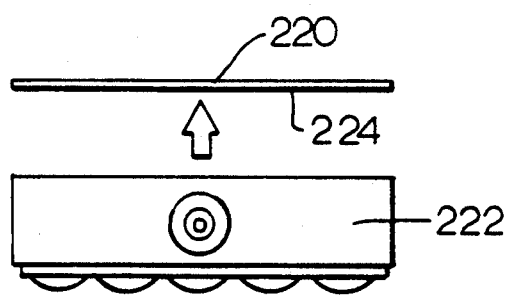
FIG. 15 is an end elevational view showing one embodiment of a cover for sealing the inventive collection cartridge until after a body fluid sample has been taken.
Figure 16:
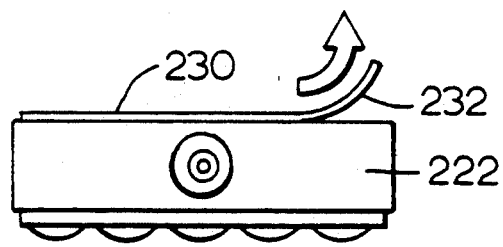
FIG. 16 is an end elevational view showing another embodiment of a cover for sealing the inventive collection cartridge until after a body fluid sample has been taken.
Figure 17:
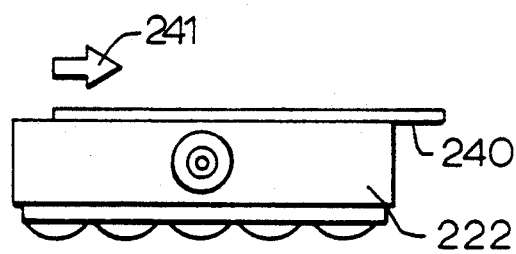
FIG. 17 is an end elevational view showing still another embodiment of a cover for sealing the inventive collection cartridge until after a body fluid sample has been taken.

As mentioned above, blood is typically drawn into the sample chamber by connecting a syringe to one end of the sample chamber and a hypodermic needle to the other end of the sample chamber. As the plunger of the syringe is withdrawn, it creates a vacuum in the sample chamber that draws blood into the needle. However, since the sample chamber must be exposed in order to allow the sensors to externally communicate with the blood in the sample chamber, the sample chamber must be enclosed while blood is being drawn into the chamber. Although the communication between the sample chamber and the sensor will generally be physical (i.e., direct contact), the communication may also be optical in the event that an optical sensor is used. The sample chambers, calibrant chambers, and blotter chambers of the previously described blood collection cartridges are preferably covered with a removable, air-permeable membrane until after blood has been collected in the cartridge. Three embodiments of blood collection cartridges utilizing an air-permeable membrane covering the chambers are illustrated in FIGS. 15-17. In FIG. 15, a rigid, air impermeable cover 220 is secured to the cartridge 222 above the chambers (not shown) by suitable means, such as a releasable adhesive coating on the surface 224 of the cover 220. In this embodiment, the cover 220 is lifted from the cartridge 222 after the blood sample has been obtained. It will be apparent that the cover 220 may be secured to the cartridge 220 by other means.

In the embodiment of FIG. 16, a flexible, air-permeable membrane 230 is secured to the cartridge 222 by a layer of adhesive coating on the membrane surface 232. The membrane 230 can be removed from the cartridge 222 after a blood sample has been obtained by peeling the membrane 230 away from the cartridge.

The embodiment of FIG. 17 utilizes a rigid, air-permeable cover 240 that is slidably mounted on the blood collection cartridge 222 by conventional means. After a blood sample has been obtained, the cover 240 is actuated in the direction of the arrow 241 to slide the cover 240 from the cartridge 222.

Figure 18A:
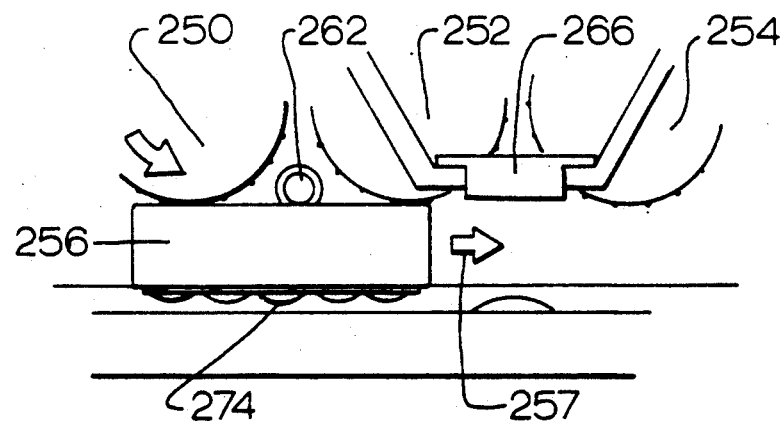
FIGS. 18A and 18B are elevational views showing one embodiment of a mechanism that can be used to analyze body fluid samples collected in the inventive fluid collecting cartridges.
Figure 18B:
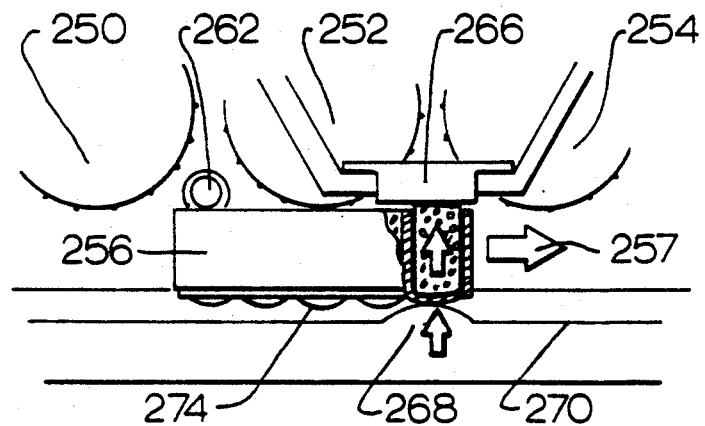

One embodiment of an apparatus for automatically scanning blood collection cartridges across a sensor or sensor array is illustrated in FIGS. 18A and 18B. The mechanism includes three rotatably driven rollers 250, 254 having sprockets formed on their outer peripheries. The sprockets are adapted to engage indexing apertures formed on the upper surface of the cartridge 256, such as, for example, indexing apertures 260, illustrated in FIG. 6. A rotatably mounted tracking roller 262 makes contact with the upper surface of the collection cartridge 256 in order to determine the location of the cartridge. The rotatably driven rollers 250, 254 advance the cartridge 256 in the direction of the arrow 257 toward a sensor assembly 266, as previously described.

With reference now to FIG. 18B, a cam surface 268 is formed on a guide surface 270 on which the car cartridge 256 slides beneath the electrode assembly 266. In the embodiment illustrated in FIGS. 18A and 18B, the chambers of the collection cartridge 256 are enclosed by a flexible membrane 274 that allows the absorbent material in the chambers to bulge outwardly from the chambers. When each of the chambers is positioned beneath the sensor array 266, the cam surface 268 forces the outwardly bulging absorbent material inwardly, thereby causing the absorbent material to bulge outwardly from the open surface of the chamber against the sensor array 266. After the first chamber is positioned beneath the sensor array 266, the driven rollers 250, 254 are rotated to advance the cartridge 256 to position the next chamber beneath the sensor array 266 until all of the chambers have been positioned beneath the sensor array 266.

Figure 19A:
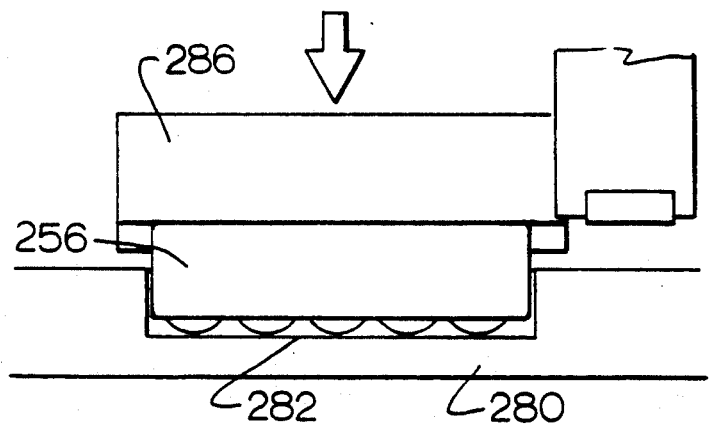
FIGS. 19A and 19B are elevational views showing another embodiment of a mechanism that can be used to analyze body fluid samples collected in the inventive fluid collecting cartridges.
Figure 19B:
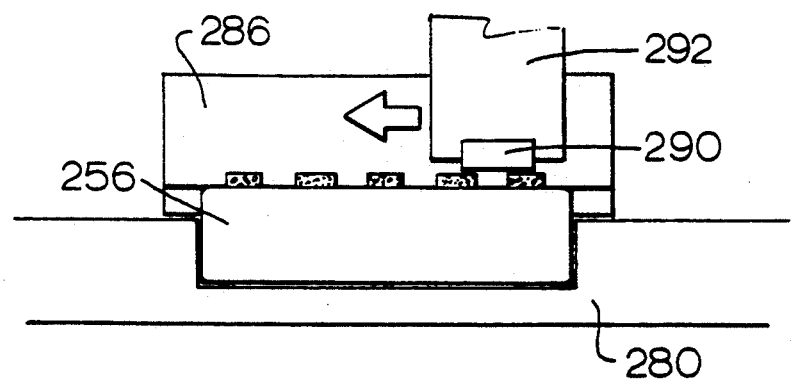

The scanning mechanism illustrated in FIGS. 18A and 18B scans the cartridge 256 across a stationary sensor array 266. It will be understood that the cartridge 256 may be stationary and the sensor array may be scanned across the stationary cartridge. As illustrated in FIGS. 19A and 19B, the cartridge 256 is positioned in a base 280 having a rectangular recess 282 adapted to receive the cartridge 256. The cartridge 256 is held stationary within the recess 282 by a downward force exerted by a retaining member 286, as illustrated in FIG. 19B. The downward force exerted by the retaining member 286 forces the downwardly bulging absorbent material in the chambers upwardly so that the absorbent material then projects upwardly from the upward surface of the cartridge. An electrode array 290 is mounted on a transversely driven electrode bracket 292 so that the electrode array 290 sequentially contacts the absorbent material projecting upwardly from each of the chambers.

Figure 20:
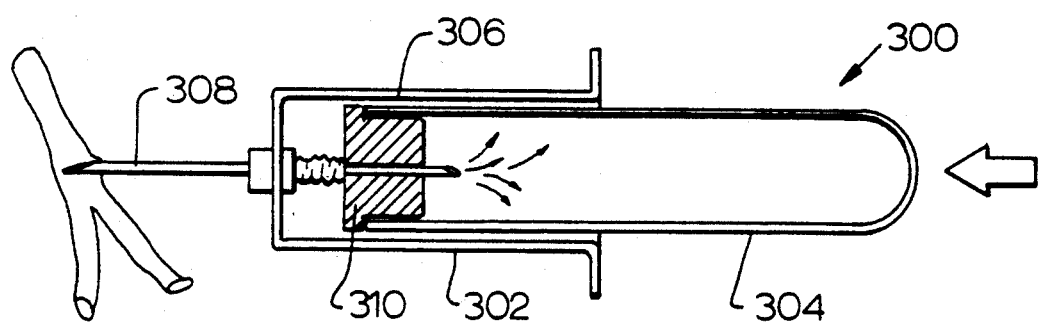
FIG. 20 is a cross-sectional view showing a conventional "VACUTAINER" device being used to obtain a blood sample.

The previously described blood collection cartridges have been illustrated as obtaining a blood sample utilizing a syringe (with the exception of the embodiment of FIG. 8). As explained in greater detail below, a blood sample may also be obtained by utilizing a vacuum in a manner similar to a conventional "VACUTAINER." As illustrated in FIG. 20, the "VACUTAINER" 300 is composed of two components, namely, an adapter 302 and a collection tube 304. The adapter 302 includes a cylindrical member 306 having a double-headed needle 308 is inserted into a blood vessel, such as a vein. The collection tube, in the form of an evacuated test tube sealed by a resilient plug 310, is then inserted into the cylindrical member 306 so that the inner end of the needle 308 punctures the plug 310 and extends into the evacuated collection tube 304. The vacuum in the tube 304 then draws blood through the needle 308 from the vein. After a sufficient quantity of blood has been collected in the tube 304, the outer end of the needle 308 is removed from the blood vessel and the collection tube 304 is removed from the cylindrical member 306. As the inner end of the needle 308 is withdrawn from the resilient cap 310, the puncture through the cap is sealed by the resilient nature of the cap 310.

Figure 21:
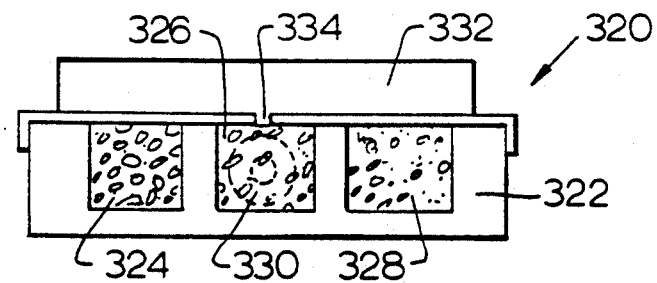
FIG. 21 is a transverse cross-sectional view of one embodiment of the inventive collection cartridge utilizing a vacuum to draw a body fluid, such as blood, from a patient.

One embodiment of a collection cartridge utilizing a vacuum to collect a blood sample is illustrated in FIG. 21. The collection cartridge 320 is formed by a generally rectangular cartridge body 322 having three chambers 324, 328 formed therein. The chambers 324, 328 contain an absorbent material saturated with a calibrating fluid, while the center chamber 326 contains a dry absorbent material which is to be saturated with the blood sample. The blood sample collection chamber 326 has a conventional Luer lock connector 330 formed at one end on which a hypodermic needle may be mounted. The blood sample collection chamber 326 is in fluid communication with a vacuum chamber 332 through a vent 334.

Figure 22:
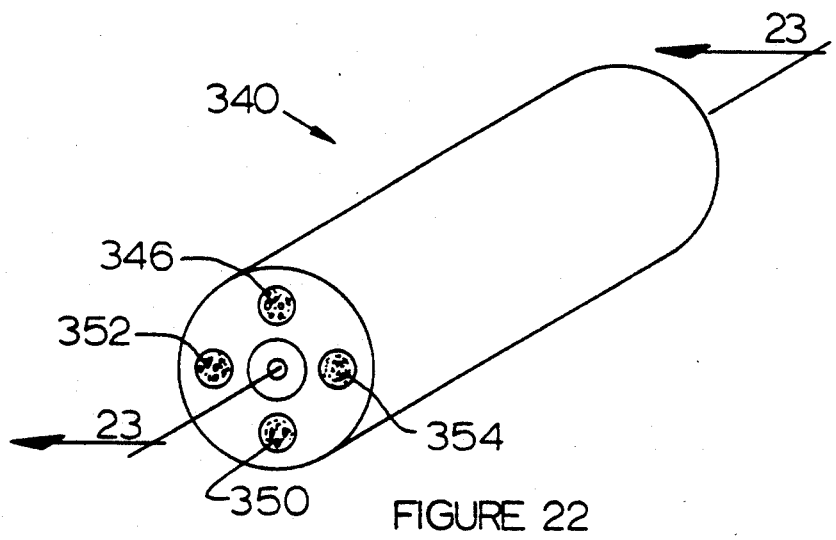
FIG. 22 is a longitudinal cross-sectional view of another embodiment of the inventive collection cartridge utilizing a vacuum to draw a body fluid, such as blood, from a patient.
Figure 23:
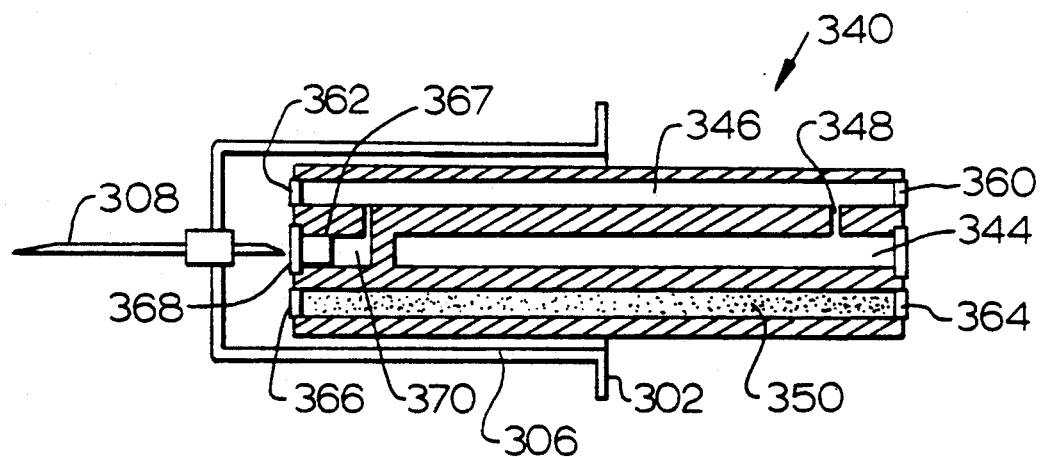
FIG. 23 is a cross-sectional view taken along the line 2222 of FIG. 22.

Another embodiment of a collection cartridge 340 using a vacuum to draw a blood sample through a needle is illustrated in FIGS. 22 and 23. The collection cartridge 340 has a cylindrical configuration that is sized to fit within the cylindrical member of a conventional "VACUTAINER" adapter 302. As best illustrated in FIG. 23, the cartridge 340 has formed therein an elongated vacuum chamber 344 extending along the axis of the cartridge 340, at least one elongated sample chamber 346 connected to the vacuum chamber 344 by a vent 348, and a chamber 350 containing a calibrating fluid. As best illustrated in FIG. 22, another chamber 352 containing a second calibrating fluid and a chamber 354 containing a washing fluid are also formed in the cartridge 340. The sample chamber is sealed by a pair of end caps 360, 362, while the calibrating chamber 350 is sealed by a pair of end caps 364, 366. An axial port 346 through a conduit 370. In the event multiple sample chambers 346 are used, they may be filled with respective dry reagents to simultaneously perform several different blood tests on the blood sample.

In use, the needle 308 of the "VACUTAINER" adapter 302 is inserted into a patient's blood vessel. The cartridge 340 is then inserted into the adapter 302 so that the inner end of the needle 308 punctures the end cap 368, thereby placing the sample chamber 346 in fluid communication with the needle 308 through the conduit 370. The vacuum applied to the sample chamber 346 through vent 348 then draws blood through the needle 308 and into the sample chamber 346. After sufficient blood has been drawn into the sample chamber 346, the cartridge 340 is removed from the adapter 302 and the needle 308 is withdrawn from the patient's blood vessel. As a result, the blood sample is drawn without the possibility of spilling blood or otherwise exposing the health care practitioner to the blood.

Figure 24:
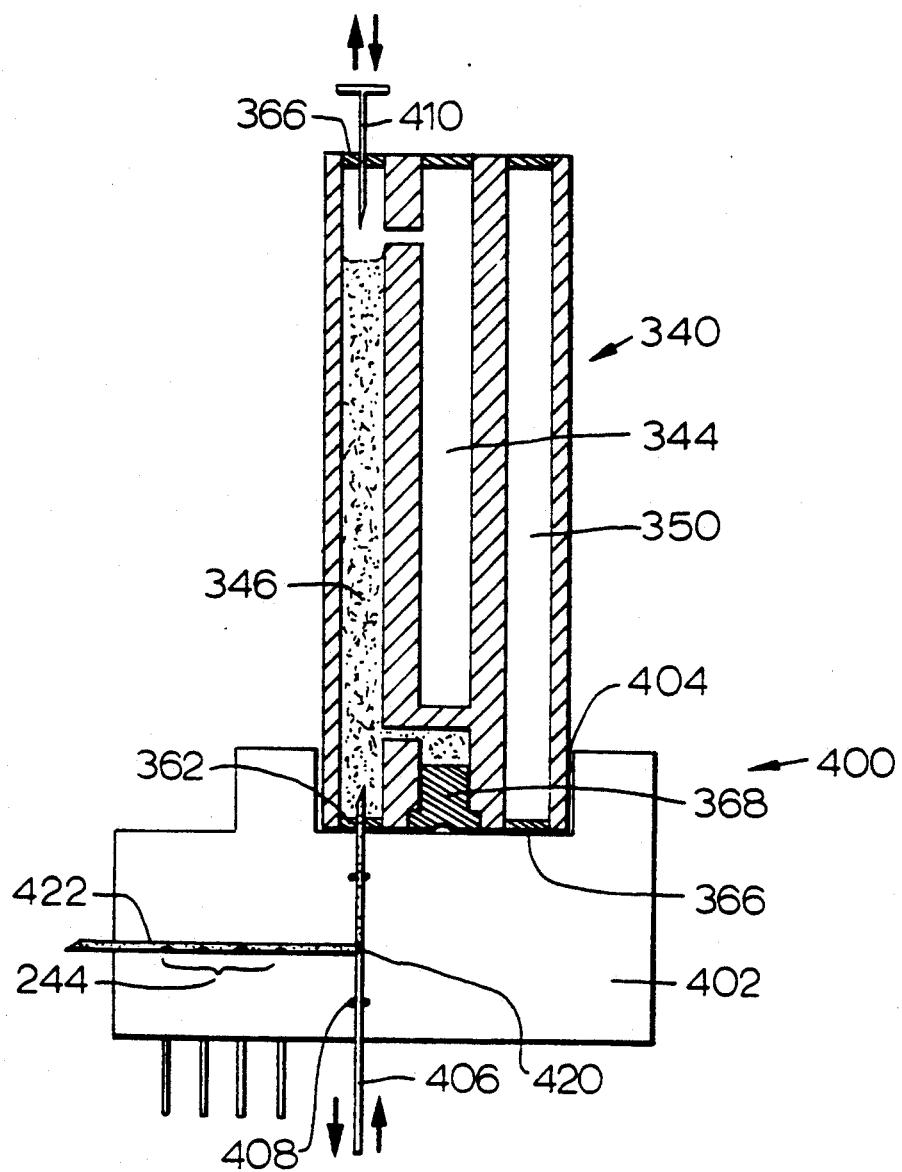
FIG. 24 is a longitudinal cross-sectional view of a mechanism for analyzing a body fluid sample obtained using the collection cartridge of FIGS. 22 and 23.

One embodiment of a mechanism for analyzing the blood sample collected in the cartridge 340 of FIGS. 22 and 23 is illustrated in FIG. 24. The mechanism 400, illustrated in FIG. 24, includes a base 402 having a cylindrical recess 404 adapted to receive the end of the cartridge 340. A needle 406 is slidably mounted in a bore formed in the base 402. An O-ring 408 tightly surrounding the needle 406 provides a fluid seal around the needle 406. In operation, after the cartridge 340 has been placed into the recess 404, the needle 406 is actuated upwardly so that its upper end punctures the resilient cap 362 enclosing the sample chamber 346. At the same time, a venting needle 410 punctures the end cap 360 sealing the other end of the sample chamber 346 so that the blood sample in the chamber 346 can flow through the needle 406 through gravity. Blood flowing downwardly through the sample chamber 346 and needle 406 passes through a hole 420 in the needle and through a conduit 422 past a plurality of sensors 244 to be analyzed as described above. After the blood sample has been analyzed, the cartridge 340 is sequentially rotated by 90 degrees until the calibrating fluid stored in both calibration chambers 352, 354 and the wash fluid stored in the chamber 350 have flowed through the conduit 422 past the sensors 244. The use of gravity to cause the blood sample to flow across the sensors 244 avoids the use of expensive pumps and valves that are costly to replace when deposits have been built up, thus making frequent replacement of all blood contacting components feasible.

Figure 25:
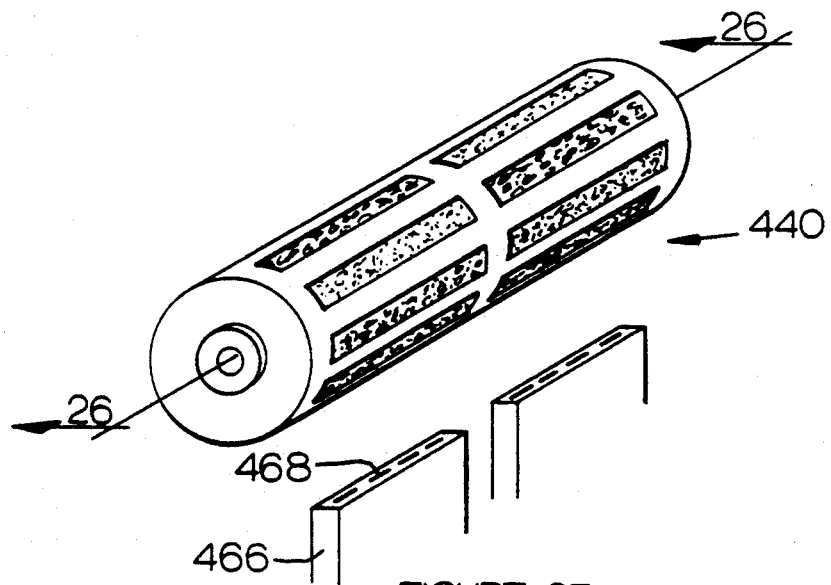
FIG. 25 is a longitudinal cross-sectional view of another embodiment of the inventive collection cartridge utilizing a vacuum to draw a body fluid, such as blood, from a patient.
Figure 26:
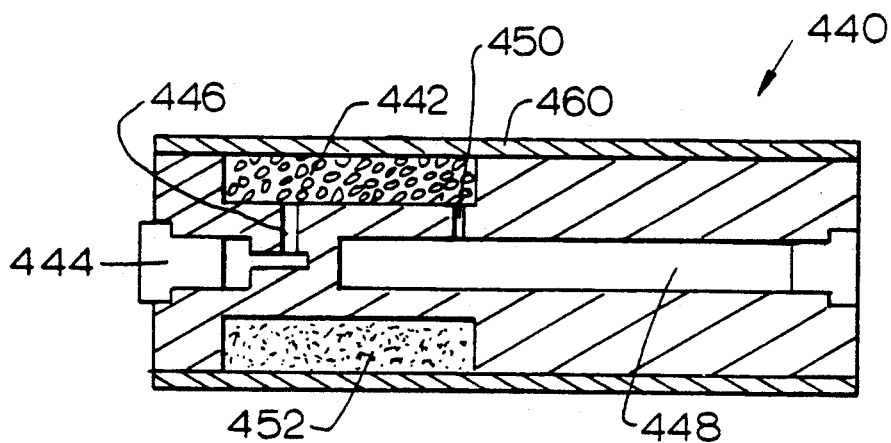
FIG. 26 is a cross-sectional view taken along the line 2626 of FIG. 25.

Another embodiment of a cylindrical collection cartridge that may be used with a "VACUTAINER" adapter is illustrated in FIGS. 25 and 26. The cartridge 440 of FIGS. 25 and 26 differs from the cartridge 340 of FIG. 24 by utilizing externally accessible chambers rather than chambers sealed by end caps as in the embodiment of FIG. 24. More specifically, with reference to FIGS. 25 and 26, the cartridge 440 has a cylindrical configuration in which a plurality of longitudinally extending, circumferentially spaced chambers are formed. A sample chamber 442 is in communication with an axial port sealed by a resilient cap 444 through a conduit 446. The sample chamber 442 communicates with an internal vacuum chamber 448 through a second conduit 450. A calibration chamber 452 is also formed in the cartridge 440. As best illustrated in FIG. 25, additional chambers are also formed in the cartridge 440 containing additional calibrating fluids, wash fluids, and drying blotters. Prior to using the cartridge 440 to take a blood sample, the cartridge 440 is surrounded by air-impermeable and somewhat resilient sleeve 460 to retain the vacuum in the vacuum chamber 448 and prevent contaminates from reaching the sample chamber 442.

After the cartridge 440 has taken a sample of blood and has been removed from the "VACUTAINER" adapter, the sleeve 460 is removed from the cartridge 440, thereby exposing the blood sample chamber 442, calibration chamber 452, and other chambers. A sensor assembly 466 (FIG. 25) having a plurality of sensors 468 formed on its end surface may then sequentially scan each of the chambers.

Figure 27:
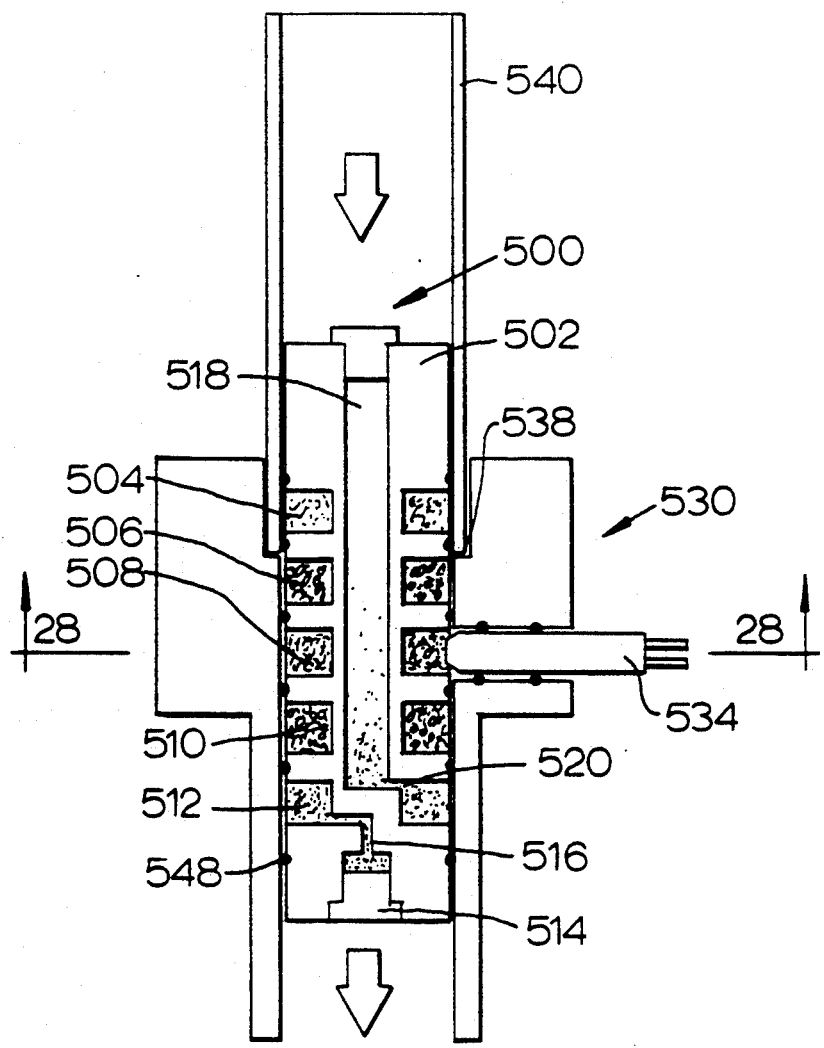
FIG. 27 is a longitudinal cross-sectional view of still another embodiment of the inventive collection cartridge utilizing a vacuum to draw a body fluid, such as blood, from a patient.
Figure 28:
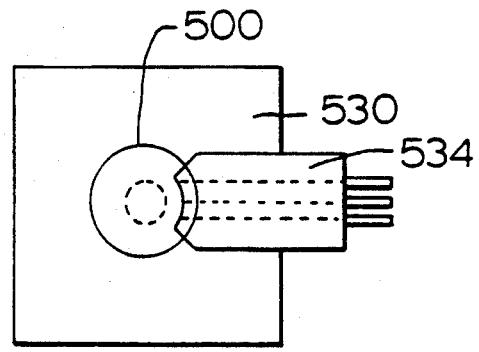
FIG. 28 is a cross-sectional view taken along the line 2828 of FIG. 27.

The cartridges 340, 440 shown in FIGS. 24–26 utilize a plurality of longitudinally extending, circumferentially spaced chambers. A cylindrical blood sample collection cartridge may also utilize annular, longitudinally spaced chambers, as illustrated in FIGS. 27 and 28. The cartridge 500 illustrated in FIGS. 27 and 28 includes a cylindrical body 502 having a plurality of annular, longitudinally spaced chambers 504, 512 formed therein. A sample chamber 512 communicates with an axial port enclosed by an end cap 514 through a conduit 516. The sample chamber 512 also communicates with an internal vacuum chamber 158 through a second conduit 520.

The collection cartridge 500 is used in the same manner as the collection cartridges of FIGS. 24–26. After the cartridge has collected a blood sample, it is inserted into an analyzing mechanism 530 having a cylindrical sleeve 532 in which a sensor assembly 534 is mounted. The cartridge 500 is inserted into the sleeve 532 in the direction designated by the arrows. A shoulder 538 formed in the sleeve 532 makes contact with an air-imprmeable sleeve 540 surrounding the cartridge 500 to maintain the vacuum in the vacuum chamber 518 until after a blood sample has been obtained. Thus, as the cartridge 500 is inserted into the sleeve 532, the sleeve 540 is automatically removed. O-rings 548 surrounding the cartridge 500 on both sides of each chamber 504, 512 prevent cross contamination between chambers.

Figure 29:
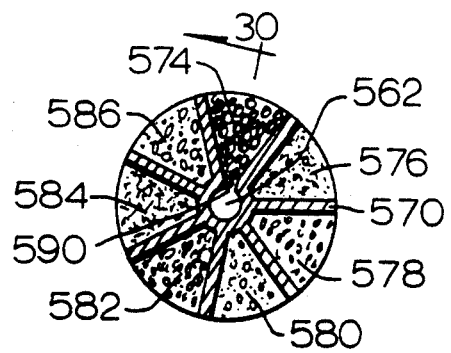
FIG. 29 is a longitudinal cross-sectional view of an embodiment of the inventive collection cartridge that is similar to the embodiment shown in FIGS. 26 and 27 except that it does not use an internal vacuum chamber to draw a body fluid into the cartridge.
Figure 30:
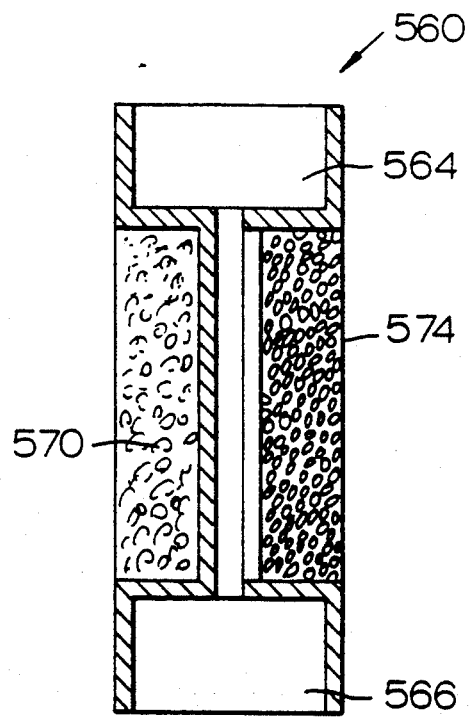
FIG. 30 is a cross-sectional view taken along the line 3030 of FIG. 29.

One embodiment of a collection cartridge that can be used with a conventional "VACUTAINER" adapter and collection tube is illustrated in FIGS. 29 and 30. The cartridge 560 is of a generally cylindrical configuration formed by a longitudinally extending tube 562 extending between cylindrical end portions 564, 566. Radially extending dividers 570 project from the conduit 562 to form a plurality of circumferentially spaced, longitudinally extending chambers 574, 586. One of the chambers 574 used as the sample chamber communicates with the interior of the conduit 562 through a vent 590. As explained in greater detail below, blood is drawn through the conduit 562, and some of the blood is absorbed into the blood sample collection chamber 574 through the vent 590.

Figure 31:
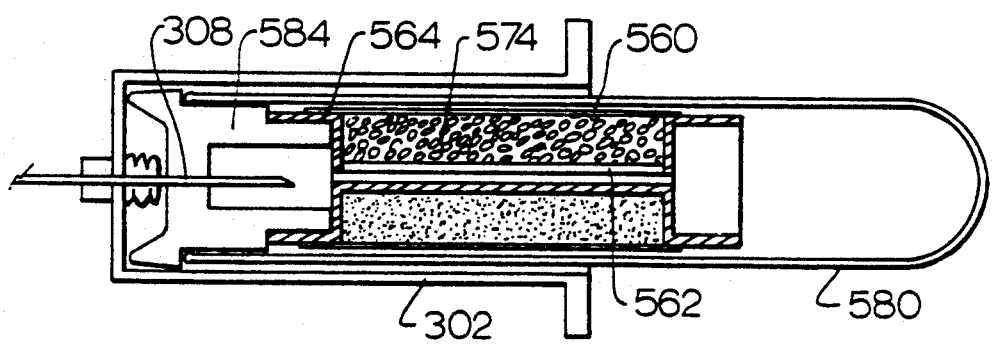
FIG. 31 is a longitudinal cross-sectional view of the collection cartridge of FIG. 29 shown being used to take a sample of a body fluid, such as blood, using a "VACUTAINER."

One technique for utilizing the cartridge 560 of FIGS. 29 and 30 is illustrated in FIG. 31. The cartridge 574 is inserted into a conventional "VACUTAINER" adapter 302 between the needle 308 and an evacuated tube 580. The vacuum from the tube 580 is coupled to the needle 308 through the conduit 562 so that blood flows through the conduit 562 to saturate the absorbent material in the blood sample collection chamber 574. In the embodiment of FIG. 31, the needle 308 extends through a resilient end cap 584 inserted into one cylindrical end portion 564 of the cartridge 560.

Figure 32:
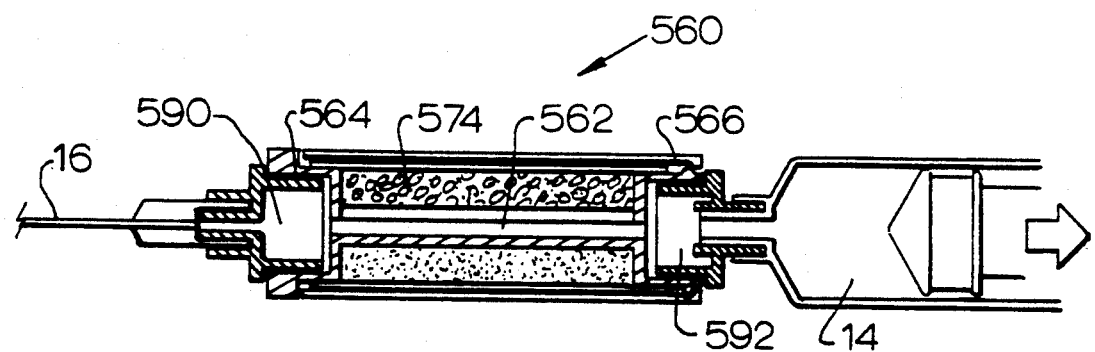
FIG. 32 is a longitudinal cross-sectional view of the collection cartridge of FIG. 29 shown being used to obtain a sample of a body fluid, such as blood, using a syringe.

Another technique for utilizing the cartridge 560 of FIG. 29 is illustrated in FIG. 32. As shown in FIG. 32, a conventional Luer connector 590 is inserted into one cylindrical end portion 564 of the cartridge 560 and a syringe 16 is mounted onto the connector 590. A similar Luer connector 592 is inserted into the other cylindrical end portion 566 of the cartridge. A syringe 14 is then attached to the Luer connector 592. When the plunger of the syringe 14 is withdrawn, blood is drawn from the needle 16 through the conduit 562 and into the syringe 14. As the blood flows through the conduit 562, some of it is absorbed in the material within the blood sample collection chamber 574.

Figure 33:
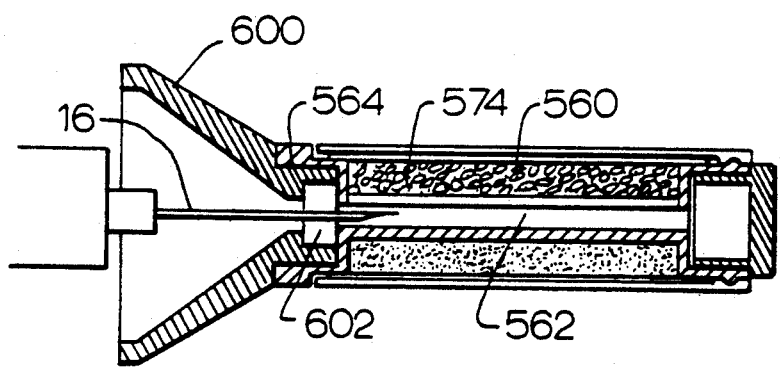
FIG. 33 is a longitudinal cross-sectional view of the collection cartridge of FIG. 29 shown being used to obtain a sample of body fluid, such as blood, by transferring the fluid from a syringe using a needle.

A final technique for utilizing the vacuum cartridge 560 of FIGS. 29 and 30 is illustrated in FIG. 33. As illustrated in FIG. 33, a syringe transfer shield 600 is inserted into one end portion 564 of the cartridge 560. The cartridge 560 has formed therein a resilient membrane 602 through which a needle 16 mounted on a syringe containing blood to be sampled is inserted. After the needle 16 has been inserted through the membrane 602 into the conduit 562, the plunger of the syringe is released to allow blood to flow through the needle 16 and into the conduit 562. Blood then flows from the conduit 562 into the sample collection chamber 574.

Figures 34A, 34B:
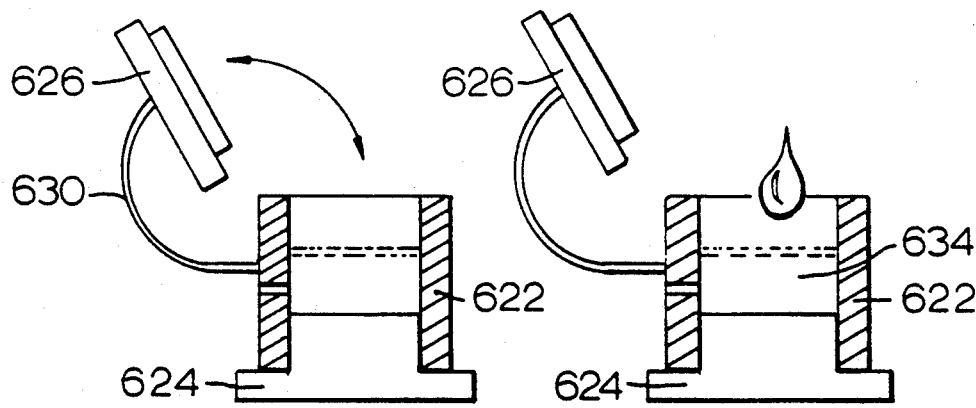
FIGS. 34A-34D are mechanical schematics of a cartridge for collecting a body fluid sample and allowing the sample to be analyzed in the collection device.
Figure 34C:
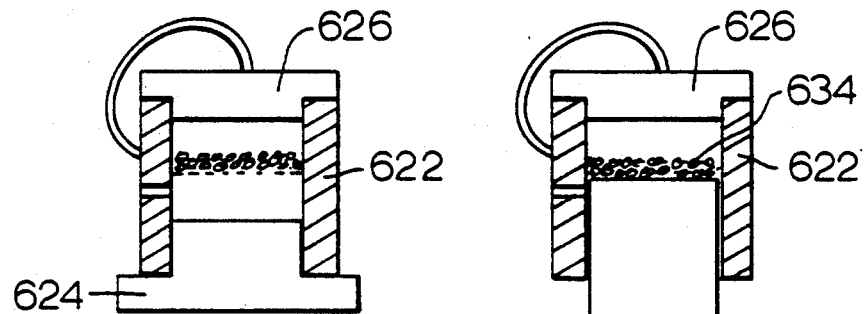
Figure 34D:
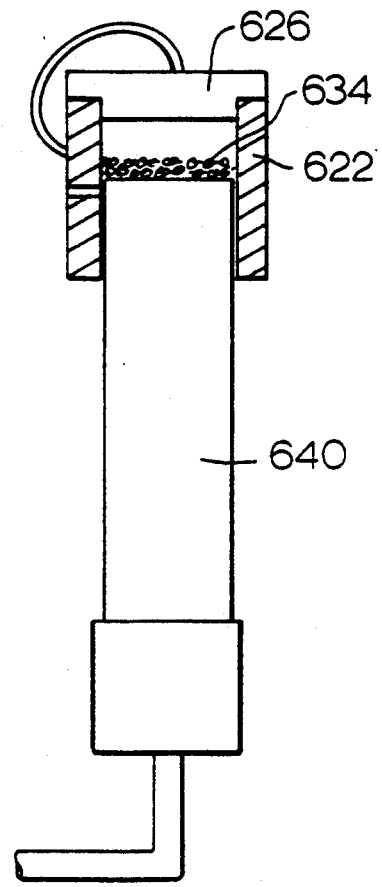

While the previously described embodiments of the invention utilize multiple chambers containing calibration fluid as well as the blood sample, a cartridge having a single chamber containing the blood sample may also be used. As illustrated in FIGS. 34A–34D, a cylindrical sampling device 620 includes a cylindrical tube 622 having its ends enclosed by a resilient end cap 624 and a second end cap 626 tethered to the cylindrical tube 622 by retaining members 630. The cap 626 is removed from the tube 622 to allow blood from a finger prick to be absorbed by a fluid absorbent material 634 in the tube 622, as illustrated in FIG. 34B. The end cap 626 is then placed over the open end of the tube 622, as illustrated in FIG. 34C, until the blood is to be analyzed. When the blood is to be analyzed, the resilient cap 624 is removed, as illustrated in FIG. 34D, and a sensor assembly 640 having one or more electrodes is inserted into the tube 622 to contact the absorbent material 634 containing the blood sample.

As mentioned above, the sample chambers in the previously described embodiments may, but need not, be filled with a fluid absorbent material to provide mechanical stability to the fluid sample. The sample chambers may also contain a reagent that reacts with the fluid sample. For example, the reagent may change color as a function of a chemical parameter of the fluid sample. The chemical parameter can then be determined using a conventional optical sensor.

It is thus seen that the inventive body fluid collection cartridge prevents fluid samples from either becoming contaminated or contaminating health care practitioners that obtain or process the sample. Furthermore, the body fluid samples contained in the collection cartridges can be analyzed without transferring the sample to another container and without the need for the sample to come into contact with internal pumps and valves commonly used in chemical analysis instruments.

We claim:

1. An apparatus for obtaining a body fluid sample and allowing said sample to be analyzing comprising:
   a generally cylindrical cartridge having at least two calibrating fluid chambers and a sample chamber, each of said chambers communicating with a respective fluid port opening on a common end-wall of said cartridge at locations that are symmetrically positioned about the axis of said cylindrical cartridge; and
   respective calibrating fluids contained in said calibrating fluid chambers.

2. The apparatus of claim 1 wherein said externally accessible fluid port for said sample chamber includes a fitting for attaching said cartridge to a needle, said cartridge further including a second externally accessible fluid port having a fitting for attaching said cartridge to a syringe, said first and second fluid ports communicating with each other through a conduit extending along the axis of said cylindrical cartridge, said axial conduit communicating with said sample chamber through a fluid vent whereby said syringe can draw said body fluid sample through said needle and axial conduit, thereby allowing said fluid sample to flow through said fluid vent into said sample chamber.

3. An apparatus for obtaining a body fluid sample and allowing said sample to be analyzed, comprising:
   a cartridge having a sample chamber, first and second calibrating fluid chambers, and first and second drying chambers positioned adjacent said first and second calibrating chambers, respectively;
   a first calibrating fluid adapted to calibrate an analyzer with which said apparatus is adapted to be used, said first calibrating fluid being contained in said first calibrating fluid chamber;
   a second calibrating fluid adapted to calibrate said analyzer at a different calibration point from said calibrating fluid, said second calibrating fluid being contained in said second calibrating fluid chamber;
   a dry, fluid absorbent material contained in said first and second drying chambers; and
   access means for allowing external access to said sample chamber, said calibrating fluid chambers and said drying chambers.

4. The apparatus of claim 3 wherein said chambers are arranged in said cartridge in the sequence of said first calibrating fluid chamber, said first drying chamber, said sample chamber, said second drying chamber, and said second calibrating fluid chamber whereby a sensor scanning across said chambers in physical contact with said chambers is dried by said dry, fluid absorbent material before and after contacting a body fluid sample in said sample chamber and after contacting said chamber containing said first calibrating fluid.

5. An apparatus for obtaining a body fluid sample and allowing said sample to be analyzed comprising:
   a cartridge having a calibrating fluid chamber and a sample chamber communicating with a first externally accessible fluid port;

a calibrating fluid contained in said calibrating fluid chamber;

a fluid absorbent material contained in said calibrating fluid chamber, said fluid absorbent material being saturated with said calibrating fluid;

a reservoir chamber communicating with said calibrating fluid chamber, said reservoir chamber containing a supply of said calibrating fluid to maintain said fluid absorbent material saturated with said calibrating fluid; and access means for allowing external access to said sample chamber and said calibrating fluid chamber.

6. An apparatus for obtaining a body fluid sample and allowing said sample to be analyzed, comprising:

a cartridge having a calibrating fluid chamber and a sample chamber communicating with a first externally accessible fluid port;

a calibrating fluid contained in said calibrating fluid chamber;

access means for allowing external access to said sample chamber and said calibrating fluid chamber;

a fitting communicating with said first externally accessible fluid port for attaching said cartridge to a needle so that said needle communicates with said sample chamber tghrough said externally accessible port; and a second externally acessible fluid port communicating with said first externally accessible fluid port through said sample chamber, said second fluid port having a fitting for attaching said cartridge to a syringe so that said syringe can draw said fluid sample into said sample chamber through said needle.

7. An apparatus for obtaining a fluid sample and allowing said sample to be analyzed comprising:

a cartridge having a calibrating fluid chamber and a sample chamber communicating with a first externally accessible fluid port;

a calibrating fluid contained in said calibrating fluid chamber;

access means for allowing external access to said sample chamber and said calibrating fluid chamber;

a fitting communicating with said first externally accessible fluid port for attaching said cartridge to a needle so that said needle communicates with said sample champer through said externally accessible port; and a second externally accessible fluid port communicating with said first externally accessible fluid port through a bypass conduit in fluid communication with said sample chamber, said second fluid port having a fitting for attaching said cartridge to a syringe so that said syringe can draw said body fluid sample through said needle and bypass conduit, threby allowing said fluid sample to flow into said sample chamber.

8. An apparatus for obtaining a fluid sample and allowing said sample to be analyzed, comprising:

a cartridge having a calibrating fluid chamber and a sample chamber communicating with a first externally accessible fluid port;

a calibrating fluid contained in said calibrating fluid chamber;

access means for allowing external access to said sample chamber and said calibrating fluid chamber;

a vacuum chamber communicating with said first externally accessible fluid port through said sample chamber land;

a resilient membrane covering said first fluid to maintain the vacuum in said vacuum chamber and said sample chamber, whereby a body fluid sample may be collected in said sample chamber by puncturing said membrane with a needle that has been placed in contact with said fluid sample.

9. The apparatus of claim 8 wherein said vacuum chamber and said sample chamber are separate chambers in fluid communication with each other through a fluid passage.

10. The apparatus of claim 9 wherein said cartridge is cylindrical and sized for insertion into a sleeve having a radially extending flange at one end and an opposite end closed by an end wall containing a double-ended hypodermic needle adapted to puncture an object, inserted into said sleeve, and wherein said first fluid port is located an one end wall of said cylindrical cartridge centered at the axis of said cylindrical cartridge so that insertion of said cartridge in said cylindrical sleeve allows the needle of said sleeve to puncture said membrane.

11. An apparatus for obtaining a fluid sample and allowing said sample to be analyzed, comprising:

a cartridge having a calibrating fluid chamber and a sample chamber communicating with a first externally accessible fluid port;

a calibrating fluid contained in said calibrating fluid chamber;

access means for allowing external access to said sample chamber and said calibrating fluid chamber; and a tapered needle shield attached to said cartridge adjacent said first externally accessible fluid port, said needle shield flaring outwardly from an aperture communicating with said first fluid port so that a needle mounted on a syringe containing a body fluid sample can be inserted into said first externally accessible fluid port to inject said fluid sample into said sample chamber.

12. An apparatus for obtaining a fluid sample and allowing said sample to be analyzed, comprising:

a cartridge having a calibrating fluid chamber and a sample chamber communicating with a first externally accessible fluid port;

a calibrating fluid contained in said calibrating fluid chamber;

access means for allowing external access to said sample chamber and said calibrating fluid chamber; and a reagent contained within said sample chamber, said reagent being chemically reactive with said body fluid sample to alter the chemical or optical properties of said reagent as a function of a chemical parameter of said fluid sample.

13. A system for obtaining and analyzing a body fluid sample, comprising:

a disposable cartridge having a sample chamber communicating with a first externally accessible fluid port through which said body fluid sample may flow into said sample chamber and a calibrating chamber containing a calibrating fluid, said cartridge further including sample means for drawing a body fluid sample into said sample chamber through said first externally accessible fluid port, and access means for allowing external access to the body fluid sample drawn into said sample chamber and the calibrating fluid contained in said calibrating chamber; and an analysis device adapted to temporarily interface with said access means to allow said body fluid sample in said sample chamber to be analyzed, said analysis device having a sensor in fluid communication with said access means to allow said fluid sample and said calibrating fluid to contact said sensor when said access means is temporarily placed in fluid communication with said sensor, said analysis device further including electoronic means connected to said sensor for providing an electrical indication of the results of an analysis of a body fluid sample in contact with said sensor whereby said analysis device can be repetitively used to analyze a large number of body fluid samples contained in respective disposable cartridges using a single reusable sensor contained in said analysis device.

14. The system of claim 13 wherein said access means includes an externally accessible opening for each of said chambers so that said chambers are externally accessible to said sensor.

15. The system of claim 14 wherein said externally accessible openings are covered by a removable membrane to seal said chambers until after said fluid sample has been drawn.

16. The system of claim 14 wherein said cartridge is of a generally planar configuration having a planar, rectangularly shaped surface on which said externally accessible openings are formed.

17. The system of claim 16 wherein said chambers have an elongated configuration and are positioned with their longitudinal axes in parallel with each other.

18. The system of claim 14, further including scanning means for causing said sensor to sequentially access each of said chambers, said scanning means including drive means for causing relative movement between said sensor and said cartridge so that said sensor is sequentially positioned adjacent each of said externally accessible openings.

19. The system of claim 18 wherein said scanning means further includes actuating means for moving said sensor and cartridge away from each other as said sensor is scanned from one externally accessbile openinng to the next and for moving said sensor and cartridge toward each other when said sensor and opening are positioned adjacent each other.

20. The system of claim 18 wherein said sensor is stationary and said drive means moves said cartridge relative to said electrode.

21. The system of claim 20 wherein said cartridge has indexing apertures formed on said planar, rectangularly shaped surface and wherein said drive means includes a rotatably driven wheel having cogs projecting from its periphery, said cogs engaging said indexing apertures to propel said cartridge across said sensor.

22. The system of claim 21 wherein said chambers are filled with a fluid absorbent material saturated with a body fluid sample or a calibrating fluid, and wherein the fluid absorbent material in said chambers bulges outwardly against a flexible membrane opposite said externally accessible openings, and wherein said cartridge slides along a planar surface having a cam surface positioned beneath said sensor, said cam surface projecting toward said sensor to contact said flexible membrane and force the outwardly bulging, fluid-absorbent material into said chambers, thereby forcing said fluid-absorbent material out of said chambers through said externally acessible openings to contact said sensor as each chamber is positioned between said cam surface and said sensor.

23. The system of claim 18 wherein said cartridge is stationary and said drive means moves said sensor relative to said cartridge.

24. The system of claim 23 wherein said cartridge is positioned on a base member and wherein said drive means includes a bracket on which said sensor is mounted and means for sequentially moving said bracket across said cartridge.

25. The system of claim 24 wherein said chambers are filled with a fluid-absorbent material saturated with a body fluid sample or a calibrating fluid, and wherein the fluid-absorbent material in said chambers bulges outwardly against a flexible membrane opposite said externally accessible openings, said scanning means further including means for forcing said cartridge away from said sensor against said base to force the outwardly bulging, fluid-absorbent material into said chambers, thereby forcing said fluid-absorbent material out of said chambers through said externally accessible openings to allow said sensor to contact said material as said sensor is positioned adjacent each of said extenally accessible openings in said chambers.

26. The system of claim 13 wherein said cartridge is of a generally cylindrical configuration.

27. The system of claim 26 wherein said chambers are symmetrically positioned about the axis of said cylindrical cartridge.

28. The system of claim 26 wherein said chambers are in the form of axially spaced annular voids formed in said cartridge.

29. The system of claim 26 wherein said access means includes an extenally accessible opening for each of said chambers so that said chambers are externally accessible to said sensor.

30. The system of claim 29 wherein said externally accessible openings are covered by a removable shield to seal said chambers until at least said body fluid sample has been drawn.

31. The system of claim 26 wherein said chambers are sealed by respective resilient membranes positioned along one axial surface of said cartridge and wherein said access means includes a needle sequentially puncturing each of said membranes to allow the fluid in its respective chamber to flow from said chamber and through said needle, said access means further including a conduit communicating with the lumen of said needle to allow said fluid sample to flow through said conduit, said sensor being mounted in said conduit so that the fluids in said chamber sequentially communicate with said sensor.

32. The system of claim 31 wherein said access means further includes means for venting each of said chambers as said needle punctures its respective membrane so that the fluid in said chamber can flow through said needle and said conduit by gravity.

33. The system of claim 13 wherein said sensor is an electrode that is sensitive to a specific chemical ion.

34. The system of claim 33, further including a plurality of electrodes, each of which is sensitive to a different chemical ion so that said system can simultaneously perform an analysis for a plurality of chemical parameters.

35. The system of claim 13, further including a plurality of sensors, each of which is sensitive to a different chemical constituent in said sample so that said system can simultaneously analyze a plurality of chemical parameters.

36. The system of claim 13, further including a reagent contained within said sample chamber, said reagent being chemically reactive with said body fluid sample to alter the chemical or optical properties of said reagent as a function of a chemical parameter of said fluid sample.

37. A method of collecting and analyzing a body fluid sample, comprising:
   collecting a plurality of body fluid samples in respective cartridges directly from respective patients,
   temporarily placing each of said cartridges in contact with an analyzer having a sensor and electronic circuitry connected to said sensor to provide an electrical indication of an analysis of a body fluid sample in communication with said sensor, said cartridges being placed in contact with said analyzer so that said sensor is in communication with said body fluid sample in said cartridge while said sample is contained in said cartridge and disposing of said cartridges.

38. The method of claim 37 wherein said cartridge further contains at least one calibrating fluid and wherein said method further includes the step of placing said sensor in contact with said calibrating fluid either before or after placing said sensor in contact with said body fluid sample.

39. The method of claim 37 wherein said cartridge is of a generally cylindrical configuration sized for insertion into a cylindrical sleeve having a radially extending flange at one end and an opposite end closed by and end wall containing a double-ended hypodermic needle adapted to puncture an object inserted into said sleeve, said cartridge having an internal sample chamber that is at least partially evacuated and in communication with an externally accessible fluid port located on one end wall of said cylindrical cartridge centered at the axis of said cylindrical cartridge, said fluid port being sealed with a resilient membrane to maintain the vacuum in said sample chamber, and wherein said sample is collected by inserting said cartridge into said cylindrical sleeve so that the needle of said sleeve punctures said membrane, thereby allowing the vacuum in said sample chamber to draw said body fluid through said first fluid port into said sample chamber.

40. The method of claim 37 wherein said ion sensor is placed in contact with said body fluid sample by inserting a needle into said cartridge to withdraw said fluid sample and allowing said fluid sample to flow from said needle across said sensor.

41. The method of claim 37 wherein said body fluid sample is stored in said cartridge in an externally accessible chamber and wherein said sensor is placed in contact with said fluid sample by placing said sensor in contact with said chamber.

42. The method of claim 41 wherein a removable membrane covers said externally accessible chamber of said cartridge, and said method further includes removing said membrane prior to placing said sensor in contact with said body fluid sample.

43. The method of claim 41 wherein said cartridge further contains a calibrating fluid and wherein said method further includes placing said sensor in contact with said calibrating fluid before or after placing said sensor in contact with said fluid sample.

44. The method of claim 37, further including simultaneously placing a plurality of sensors electrodes in contact with said body fluid sample while said fluid sample is contained in said cartridge.

45. The method of claim 37 wherein said sensor is an ion sensitive electrode.

46. The system of claim 13 wherein said cartridge further includes a fluid absorbent material contained in said sample chamber and said calibrating fluid chamber, said fluid absorbent material absorbing said body fluid sample and said calibrating fluid to retain said body fluid sample and said calibrating fluid in said cartridge.

47. The system of claim 13 wherein said cartridge further includes a second calibrating chamber containing a second calibrating fluid, and wherein said access means further allows external access to said second calibrating fluid in said second calibration chamber.

48. The system of claim 13 wherein said access means includes a port in said sample chamber through which said sensor is adapted for insertion into said sample chamber to make contact with said body fluid sample contained therein.

49. The system of claim 48 wherein said port through which said sensor is adapted for insertion is said first externally accessible fluid port.

50. The system of claim 13 wherein said access means includes a port in said calibrating chamber through which said sensor is adapted for insertion into said calibration chamber to make contact with said calibrating fluid contained therein.

51. The system of claim 13 wherein said sample means includes a second fluid port communicating with said sample chamber, and means for creating a vacuum at said second fluid port to draw said body fluid sample into said sample chamber through said first fluid port.

52. The system of claim 51 wherein said means for creating a vacuum at said second fluid port includes a syringe coupled to said second fluid port.

53. The method of claim 37 wherein said body fluid samples are collected in said cartridges by the method of:
   placing said body fluid sample in fluid communication with a sample chamber in said cartridge; and
   applying a vacuum to said sample fluid chamber thereby drawing said body fluid sample into said cartridge.

54. The method of claim 37 wherein said sensor is placed in communication with said body fluid sample by inserting said sensor through a port in said cartridge into said cartridge to physically contact said body fluid sample.

55. The method of claim 37 wherein said cartridge further contains a calibrating fluid, and wherein said method further includes placing said sensor in contact with said calibrating fluid before or after placing said sensor in contact with said fluid sample.

* * * * *